US008586624B2

(12) United States Patent
Sun

(10) Patent No.: US 8,586,624 B2
(45) Date of Patent: Nov. 19, 2013

(54) THIOPHENE INHIBITORS OF S-NITROSOGLUTATHIONE REDUCTASE

(75) Inventor: Xicheng Sun, Broomfield, CO (US)

(73) Assignee: N30 Pharmaceuticals, Inc., Boulder, CO (US)

( * ) Notice: Subject to any disclaimer, the term of this patent is extended or adjusted under 35 U.S.C. 154(b) by 0 days.

(21) Appl. No.: 13/513,864

(22) PCT Filed: Dec. 14, 2010

(86) PCT No.: PCT/US2010/060303
§ 371 (c)(1),
(2), (4) Date: Jun. 5, 2012

(87) PCT Pub. No.: WO2011/075478
PCT Pub. Date: Jun. 23, 2011

(65) Prior Publication Data
US 2012/0245210 A1    Sep. 27, 2012

Related U.S. Application Data

(60) Provisional application No. 61/286,881, filed on Dec. 16, 2009.

(51) Int. Cl.
*A61K 31/381* (2006.01)
*C07D 333/06* (2006.01)

(52) U.S. Cl.
USPC ............ 514/438; 548/311.1; 549/59; 549/79; 514/397; 514/444

(58) Field of Classification Search
USPC ............ 548/311.1; 549/59, 79; 514/397, 438, 514/444
See application file for complete search history.

(56) References Cited

U.S. PATENT DOCUMENTS

| 3,743,656 | A | 7/1973 | Brown et al. | |
|---|---|---|---|---|
| 6,627,647 | B1 | 9/2003 | Betageri | |
| 7,030,153 | B2 * | 4/2006 | Talley et al. | 514/438 |
| 2002/0045605 | A1 | 4/2002 | Kargman et al. | |
| 2002/0128205 | A1 | 9/2002 | Stamler et al. | |
| 2005/0014697 | A1 | 1/2005 | Stamler et al. | |
| 2005/0187166 | A1 | 8/2005 | Stamler et al. | |
| 2010/0286174 | A1 | 11/2010 | Stamler et al. | |

FOREIGN PATENT DOCUMENTS

| EP | 0853083 | 7/1998 |
|---|---|---|
| EP | 1279689 | 10/2008 |
| WO | WO 95/00501 | 1/1995 |
| WO | WO 01/39769 | 6/2001 |
| WO | WO 03/044015 | 5/2003 |
| WO | WO 2005/000229 | 1/2005 |
| WO | WO 2006/020884 | 2/2006 |
| WO | WO 2007/009083 | 1/2007 |
| WO | WO 2007/028145 | 3/2007 |
| WO | WO 2007/098923 | 9/2007 |
| WO | WO 2009/076665 | 6/2009 |
| WO | WO 2010/107476 | 9/2010 |

OTHER PUBLICATIONS de Belder et al. (May 1994) "Effects of S-nitroso-glutathione in the human forearm circulation; evidence for selective inhibition of platelet activation", *Cardiovasc Res.*, 28(5):691-694.
de Jesus-Berrios et al. (Nov. 2003) "Enzymes that Counteract Nitrosative Stress Promot Fungal Virulence", *Curr. Biol.*, 13:1963-1968.
Foster et al. (Apr. 2003) "S-nitrosylation in health and disease", *Trends in Molecular Medicine*, 9(4):160-168.
Gaston et al. (Dec. 1993) "Endogenous nitrogen oxides and bronchodilator S-nitrosolthiols in human airways", *Proc. Natl. Acad. Sci. USA*, 90:10957-10961.
Gauthier et al., Bioorganic & Medicinal Chemistry Letters (1996), 6(1), 87-92, "Synthesis and biological evaluation of 2,3-diarylthiophenes as selective Cox-2 inhibitors. Part II. Replacing the heterocycle."
International Preliminary Report on Patentability issued in PCT/US2010/060303 mailed Jun. 19, 2012.
International Search Report and Written Opinion issued in PCT/US2010/060303 mailed Feb. 23, 2011.
Jensen et al. (1998) "S-Nitrosoglutathione is a substrate for rat alcohol dehydrognease class III isoenzyme", *Biochem J.*, 331:659-668.
Kaposzta et al. (2002) "S-Nitrosoglutathione Reduces Asymptomatic Embolization After Carotid Angioplasty", *Circulation*, 106(24):3057-3062.
Lipton et al. (Sep. 2001) "S-Nitrosothiols signal the ventilatory response to hypoxia", *Nature*, 413:171-174.
Liu et al. (Feb. 2004) "Essential Roles of S-Nitrosothiols in Vascular Homeostatsis and Endotoxic Shock", *Cell*, 116(4):617-628.
Liu et al. (Mar. 2001) "A metabolic enzyme for S-nitrosothiol conserved from bacterial to humans", *Nature*, 410:490-494.
Que et al. (Jun. 2005) "Protection from Experimental Asthma by an Endogenous Bronchodilator", *Science*, 308(5728):1618-1621.
Sanghani et al. (2000) "Kinetic Mechanism of Human Glutathioone-Dependent Formaldehyde Dehydrogenase", *Biochemistry*, 39:10720-10729.
Sanghani et al. (2002) "Human Glutathione-Dependent Formaldehyde Dehydrognease. Structures of Apo, Binary, and Inhibitory Ternary Complexes", *Biochemistry*, 41:10778-10786.
Staab et al. (2008) "Dual functions of alcohol dehydrogenase 3: implications with focus on formaldehyde dehydrogenase and S-nitroglutathione reductase activities", *Cell Mol. Life Sci*, 65:3950-3960.
Staab et al. (Jun. 15, 2009) "Medium-chain fatty acids and glutathione derivatives as inhibitors of S-nitrosoglutathione reduction mediated by alcohol dehydrogenase 3", Chemico-Biological Interactions 180(1):113-118.
Stamler et al. (Aug. 1992) "Nitric oxide circulates in mammalian plasma primarily as an S-nitrose adduct of serium albumin", *Proc. Natl. Acad. Sci. USA*, 89:7674-7677.

(Continued)

*Primary Examiner* — Kamal Saeed
*Assistant Examiner* — Janet L Coppins
(74) *Attorney, Agent, or Firm* — Swanson & Bratschun, L.L.C.

(57) ABSTRACT

The present invention is directed to novel thiophene inhibitors of S-nitrosoglutathione reductase (GSNOR), pharmaceutical compositions comprising such GSNOR inhibitors, and methods of making and using the same.

18 Claims, No Drawings

(56) References Cited

OTHER PUBLICATIONS

Uotila and Koivusalo (1989) Coenzymes and Cofactors vol. 3: Glutathione, part A., D. Dolphin, ed. pp. 517-551 (New York, John Wiley & Sons).

Zaman et al. (2001) "S-Nitrosoglutathione Increases Cystic Fibrosis Transmembrane Regulator Maturation", *Biochem Biophys Res Commun.*, 284:65-70.

European Search Opinion issued Apr. 23, 2013 in EP application serial No. 10838203.7.

* cited by examiner

THIOPHENE INHIBITORS OF S-NITROSOGLUTATHIONE REDUCTASE

RELATED APPLICATIONS

This application is a 35 U.S.C. §371 national phase application of PCT/US2010/060303, filed Dec. 14, 2010 (WO 2011/075478), entitled "Novel Thiophene Inhibitors of S-Nitrosoglutathione Reductase." PCT/US2010/060303 claims the benefit of U.S. Provisional Application Ser. No. 61/286,881, filed Dec. 16, 2009, which is incorporated herein by reference in its entirety.

FIELD OF THE INVENTION

The present invention is directed to novel thiophene compounds, pharmaceutical compositions comprising such compounds, and methods of making and using the same. These compounds are useful as inhibitors of S-nitrosoglutathione reductase (GSNOR).

BACKGROUND

The chemical compound nitric oxide is a gas with chemical formula NO. NO is one of the few gaseous signaling molecules known in biological systems, and plays an important role in controlling various biological events. For example, the endothelium uses NO to signal surrounding smooth muscle in the walls of arterioles to relax, resulting in vasodilation and increased blood flow to hypoxic tissues. NO is also involved in regulating smooth muscle proliferation, platelet function, and neurotransmission, and plays a role in host defense. Although NO is highly reactive and has a lifetime of a few seconds, it can both diffuse freely across membranes and bind to many molecular targets. These attributes make NO an ideal signaling molecule capable of controlling biological events between adjacent cells and within cells.

NO is a free radical gas, which makes it reactive and unstable, thus NO is short lived in vivo, having a half life of 3-5 seconds under physiologic conditions. In the presence of oxygen, NO can combine with thiols to generate a biologically important class of stable NO adducts called S-nitrosothiols (SNO's). This stable pool of NO has been postulated to act as a source of bioactive NO and as such appears to be critically important in health and disease, given the centrality of NO in cellular homeostasis (Stamler et al., *Proc. Natl. Acad. Sci. USA*, 89:7674-7677 (1992)). Protein SNO's play broad roles in the function of cardiovascular, respiratory, metabolic, gastrointestinal, immune, and central nervous system (Foster et al., *Trends in Molecular Medicine*, 9 (4):160-168, (2003). One of the most studied SNO's in biological systems is S-nitrosoglutathione (GSNO) (Gaston et al., *Proc. Natl. Acad. Sci. USA* 90:10957-10961 (1993)), an emerging key regulator in NO signaling since it is an efficient transnitrosating agent and appears to maintain an equilibrium with other S-nitrosated proteins (Liu et al., *Nature*, 410:490-494 (2001)) within cells. Given this pivotal position in the NO—SNO continuum, GSNO provides a therapeutically promising target to consider when NO modulation is pharmacologically warranted.

In light of this understanding of GSNO as a key regulator of NO homeostasis and cellular SNO levels, studies have focused on examining endogenous production of GSNO and SNO proteins, which occurs downstream from the production of the NO radical by the nitric oxide synthetase (NOS) enzymes. More recently there has been an increasing understanding of enzymatic catabolism of GSNO which has an important role in governing available concentrations of GSNO and consequently available NO and SNO's.

Central to this understanding of GSNO catabolism, researchers have recently identified a highly conserved S-nitrosoglutathione reductase (GSNOR) (Jensen et al., *Biochem J.*, 331:659-668 (1998); Liu et al., (2001)). GSNOR is also known as glutathione-dependent formaldehyde dehydrogenase (GSH-FDH), alcohol dehydrogenase 3 (ADH-3) (Uotila and Koivusalo, *Coenzymes and Cofactors.*, D. Dolphin, ed. pp. 517-551 (New York, John Wiley & Sons, (1989)), and alcohol dehydrogenase 5 (ADH-5) Importantly GSNOR shows greater activity toward GSNO than other substrates (Jensen et al., 1998; Liu et al., 2001) and appears to mediate important protein and peptide denitrosating activity in bacteria, plants, and animals. GSNOR appears to be the major GSNO-metabolizing enzyme in eukaryotes (Liu et al., 2001). Thus, GSNO can accumulate in biological compartments where GSNOR activity is low or absent (e.g., airway lining fluid) (Gaston et al., 1993).

Yeast deficient in GSNOR accumulate S-nitrosylated proteins which are not substrates of the enzyme, which is strongly suggestive that GSNO exists in equilibrium with SNO-proteins (Liu et al., 2001). Precise enzymatic control over ambient levels of GSNO and thus SNO-proteins raises the possibility that GSNO/GSNOR may play roles across a host of physiological and pathological functions including protection against nitrosative stress wherein NO is produced in excess of physiologic needs. Indeed, GSNO specifically has been implicated in physiologic processes ranging from the drive to breathe (Lipton et al., *Nature*, 413:171-174 (2001)) to regulation of the cystic fibrosis transmembrane regulator (Zaman et al., *Biochem Biophys Res Commun*, 284: 65-70 (2001)), to regulation of vascular tone, thrombosis, and platelet function (de Belder et al., *Cardiovasc Res.;* 28(5): 691-4 (1994)); Z. Kaposzta, et al., *Circulation;* 106(24): 3057-3062, (2002)) as well as host defense (de Jesus-Berrios et al., *Curr. Biol.*, 13:1963-1968 (2003)). Other studies have found that GSNOR protects yeast cells against nitrosative stress both in vitro (Liu et al., 2001) and in vivo (de Jesus-Berrios et al., (2003)).

Collectively, data suggest GSNO as a primary physiological ligand for the enzyme S-nitrosoglutathione reductase (GSNOR), which catabolizes GSNO and consequently reduces available SNO's and NO in biological systems (Liu et al., (2001)), (Liu et al., *Cell*, 617-628 (2004)), and (Que et al., *Science*, 308, (5728):1618-1621 (2005)). As such, this enzyme plays a central role in regulating local and systemic bioactive NO. Since perturbations in NO bioavailability has been linked to the pathogenesis of numerous disease states, including hypertension, atherosclerosis, thrombosis, asthma, gastrointestinal disorders, inflammation, and cancer, agents that regulate GSNOR activity are candidate therapeutic agents for treating diseases associated with NO imbalance.

Nitric oxide (NO), S-nitrosoglutathione (GSNO), and S-nitrosoglutathione reductase (GSNOR) regulate normal lung physiology and contribute to lung pathophysiology. Under normal conditions, NO and GSNO maintain normal lung physiology and function via their anti-inflammatory and bronchodilatory actions. Lowered levels of these mediators in pulmonary diseases such as asthma, chronic obstructive pulmonary disease (COPD) may occur via up-regulation of GSNOR enzyme activity. These lowered levels of NO and GSNO, and thus lowered anti-inflammatory capabilities, are key events that contribute to pulmonary diseases and which can potentially be reversed via GSNOR inhibition.

Inflammatory bowel diseases (IBD's), including Crohn's and ulcerative colitis, are chronic inflammatory disorders of the gastrointestinal (GI) tract, in which NO, GSNO, and GSNOR can exert influences. Under normal conditions, NO and GSNO function to maintain normal intestinal physiology via anti-inflammatory actions and maintenance of the intestinal epithelial cell barrier. In IBD, reduced levels of GSNO and NO are evident and likely occur via up-regulation of GSNOR activity. The lowered levels of these mediators contribute to the pathophysiology of IBD via disruption of the epithelial barrier via dysregulation of proteins involved in maintaining epithelial tight junctions. This epithelial barrier dysfunction, with the ensuing entry of micro-organisms from the lumen, and the overall lowered anti-inflammatory capabilities in the presence of lowered NO and GSNO, are key events in IBD progression that can be potentially influenced by targeting GSNOR.

Currently, there is a great need in the art for diagnostics, prophylaxis, ameliorations, and treatments for medical conditions relating to increased NO synthesis and/or increased NO bioactivity. In addition, there is a significant need for novel compounds, compositions, and methods for preventing, ameliorating, or reversing other NO-associated disorders. The present invention satisfies these needs.

SUMMARY

The present invention provides novel thiophene compounds. These compounds are useful as S-nitrosoglutathione reductase ("GSNOR") inhibitors. The invention encompasses pharmaceutically acceptable salts, stereoisomers, prodrugs, and metabolites of the described compounds. Also encompassed by the invention are pharmaceutical compositions comprising at least one compound of the invention and at least one pharmaceutically acceptable carrier.

The compositions of the present invention can be prepared in any suitable pharmaceutically acceptable dosage form.

The present invention provides a method for inhibiting GSNOR in a subject in need thereof. Such a method comprises administering a therapeutically effective amount of a pharmaceutical composition comprising at least one GSNOR inhibitor or a pharmaceutically acceptable salt, prodrug, stereoisomer, or metabolite thereof, in combination with at least one pharmaceutically acceptable carrier. The GSNOR inhibitor can be a novel compound according to the invention, or it can be a known compound which previously was not known to be an inhibitor of GSNOR.

The present invention also provides a method of treating a disorder ameliorated by NO donor therapy in a subject in need thereof. Such a method comprises administering a therapeutically effective amount of a pharmaceutical composition comprising at least one GSNOR inhibitor or a pharmaceutically acceptable salt, stereoisomer, prodrug, or metabolite thereof, in combination with at least one pharmaceutically acceptable carrier. The GSNOR inhibitor can be a novel compound according to the invention, or it can be a known compound which previously was not known to be an inhibitor of GSNOR.

The present invention also provides a method of treating a cell proliferative disorder in a subject in need thereof. Such a method comprises administering a therapeutically effective amount of a pharmaceutical composition comprising at least one GSNOR inhibitor or a pharmaceutically acceptable salt, stereoisomer, prodrug or metabolite thereof, in combination with at least one pharmaceutically acceptable carrier. The GSNOR inhibitor can be a novel compound according to the invention, or it can be a known compound which previously was not known to be an inhibitor of GSNOR.

The methods of the invention encompass administration with one or more secondary active agents. Such administration can be sequential or in a combination composition.

Although methods and materials similar or equivalent to those described herein can be used in the practice or testing of the present invention, suitable methods and materials are described below. All publicly available publications, patent applications, patents, and other references mentioned herein are incorporated by reference in their entirety. In the case of conflict, the present specification, including definitions, will control.

Both the foregoing summary and the following detailed description are exemplary and explanatory and are intended to provide further details of the compositions and methods as claimed. Other objects, advantages, and novel features will be readily apparent to those skilled in the art from the following detailed description.

DETAILED DESCRIPTION

A. Overview of the Invention

Until recently, S-nitrosoglutathione reductase (GSNOR) was known to oxidize the formaldehyde glutathione adduct, S-hydroxymethylglutathione. GSNOR has since been identified in a variety of bacteria, yeasts, plants, and animals and is well conserved. The proteins from *E. coli*, *S. cerevisiae* and mouse macrophages share over 60% amino acid sequence identity. GSNOR activity (i.e., decomposition of GSNO when NADH is present as a required cofactor) has been detected in *E. coli*, in mouse macrophages, in mouse endothelial cells, in mouse smooth muscle cells, in yeasts, and in human HeLa, epithelial, and monocyte cells. Human GSNOR nucleotide and amino acid sequence information can be obtained from the National Center for Biotechnology Information (NCBI) databases under Accession Nos. M29872, NM_000671. Mouse GSNOR nucleotide and amino acid sequence information can be obtained from NCBI databases under Accession Nos. NM_007410. In the nucleotide sequence, the start site and stop site are underlined. CDS designates coding sequence. SNP designates single nucleotide polymorphism. Other related GSNOR nucleotide and amino acid sequences, including those of other species, can be found in U.S. Patent Application 2005/0014697.

In accord with the present invention, GSNOR has been shown to function in vivo and in vitro to metabolize S-nitrosoglutathione (GSNO) and protein S-nitrosothiols (SNOs) to modulate NO bioactivity, by controlling the intracellular levels of low mass NO donor compounds and preventing protein nitrosylation from reaching toxic levels.

Based on this, it follows that inhibition of this enzyme potentiates bioactivity in diseases in which NO donor therapy is indicated, inhibits the proliferation of pathologically proliferating cells, and increases NO bioactivity in diseases where this is beneficial.

The present invention provides pharmaceutical agents that are potent inhibitors of GSNOR. In particular, provided are substituted thiophene analogs that are inhibitors of GSNOR having the structure depicted below (Formula I), or a pharmaceutically acceptable salt, stereoisomer, prodrug, or metabolite thereof.

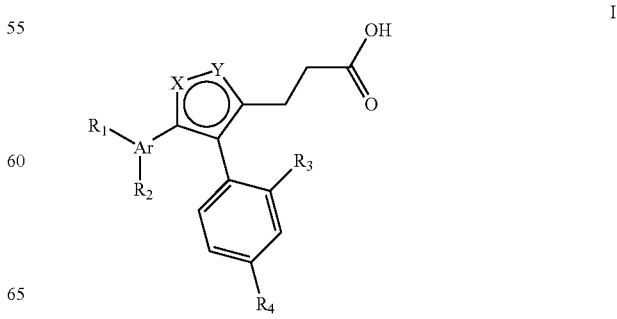

wherein:

X and Y are selected from the group consisting of S or CH, provided that when X is S, Y must be CH and when X is CH, Y must be S;

Ar is selected from the group consisting of phenyl and thiophen-yl;

$R_1$ is selected from the group consisting of hydrogen, unsubstituted imidazolyl, substituted imidazolyl, carbamoyl, chloro, bromo, fluoro, hydroxy, and methoxy;

$R_2$ is selected from the group consisting of hydrogen, methyl, chloro, fluoro, hydroxy, methoxy, ethoxy, propoxy, carbamoyl, dimethylamino, amino, formamido, and trifluoromethyl;

$R_3$ is selected from the group consisting of hydrogen, methyl, methoxy, chloro, and fluoro; and $R_4$ is selected from the group consisting of $CONH_2$, $NHSO_2CH_3$, hydroxy, chloro, and substituted and unsubstituted imidazolyl.

As used in this context, the term "analog" refers to a compound having similar chemical structure and function as compounds of Formula I that retains the thiophene ring.

Some thiophene analogs of the invention can also exist in various isomeric forms, including configurational, geometric, and conformational isomers, as well as existing in various tautomeric forms, particularly those that differ in the point of attachment of a hydrogen atom. As used herein, the term "isomer" is intended to encompass all isomeric forms of a compound including tautomeric forms of the compound.

Illustrative compounds having asymmetric centers can exist in different enantiomeric and diastereomeric forms. A compound can exist in the form of an optical isomer or a diastereomer. Accordingly, the invention encompasses compounds in the forms of their optical isomers, diastereomers and mixtures thereof, including racemic mixtures.

It should be noted that if there is a discrepancy between a depicted structure and a name given to that structure, the depicted structure controls. In addition, if the stereochemistry of a structure or a portion of a structure is not indicated with, for example, bold, wedged, or dashed lines, the structure or portion of the structure is to be interpreted as encompassing all stereoisomers of the described compound.

B. S-Nitrosoglutathione Reductase Inhibitors

1. Inventive Compounds

In one of its aspects the present invention provides a compound having a structure shown in Formula I, or a pharmaceutically acceptable salt, stereoisomer, prodrug or metabolite

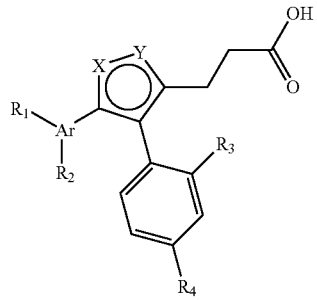

I wherein:

X and Y are selected from the group consisting of S or CH, provided that when X is S, Y must be CH and when X is CH, Y must be S;

Ar is selected from the group consisting of phenyl and thiophen-yl;

$R_1$ is selected from the group consisting of hydrogen, unsubstituted imidazolyl, substituted imidazolyl, carbamoyl, chloro, bromo, fluoro, hydroxy, and methoxy;

$R_2$ is selected from the group consisting of hydrogen, methyl, chloro, fluoro, hydroxy, methoxy, ethoxy, propoxy, carbamoyl, dimethylamino, amino, formamido, and trifluoromethyl; and $R_3$ is selected from the group consisting of hydrogen, methyl, methoxy, chloro, and fluoro; and $R_4$ is selected from the group consisting of $CONH_2$, $NHSO_2CH_3$, hydroxy, chloro, and substituted and unsubstituted imidazolyl.

In a further aspect of the invention, Ar is selected from the group consisting of

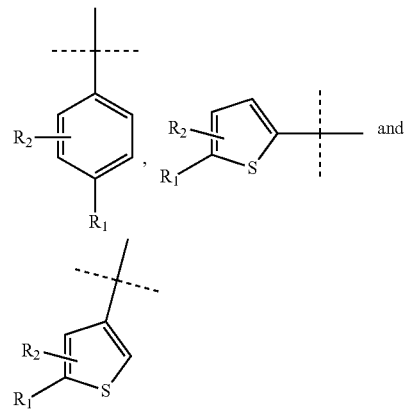

wherein $R_1$ and $R_2$ are as defined previously.

In a further aspect of the invention, $R_1$ is

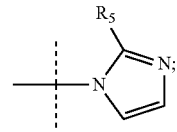

wherein $R_5$ is selected from the group consisting of hydrogen, methyl, and ethyl.

In a further aspect of the invention, $ArR_1R_2$ is selected from the group consisting of: 4-methoxyphenyl, 4-chloro-2-methoxyphenyl, 4-hydroxyphenyl, 4-carbamoylphenyl, and 4-bromophenyl.

In a further aspect of the invention, $R_3$ is selected from the group consisting of hydrogen, methyl, and methoxy.

In one of its aspects the present invention provides a compound having a structure shown in Formula II, or a pharmaceutically acceptable salt, stereoisomer, prodrug or metabolite thereof:

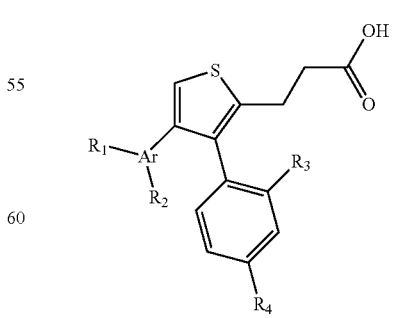

II wherein:

Ar is selected from the group consisting of phenyl and thiophen-yl;

$R_1$ is selected from the group consisting of hydrogen, unsubstituted imidazolyl, substituted imidazolyl, carbamoyl, chloro, bromo, fluoro, hydroxy, and methoxy;

$R_2$ is selected from the group consisting of hydrogen, methyl, chloro, fluoro, hydroxy, methoxy, ethoxy, propoxy, carbamoyl, dimethylamino, amino, formamido, and trifluoromethyl; and $R_3$ is selected from the group consisting of hydrogen, methyl, methoxy, chloro, and fluoro; and $R_4$ is selected from the group consisting of $CONH_2$, $NHSO_2CH_3$, hydroxy, chloro, and substituted and unsubstituted imidazolyl.

In a further aspect of the invention, Ar is selected from the group consisting of

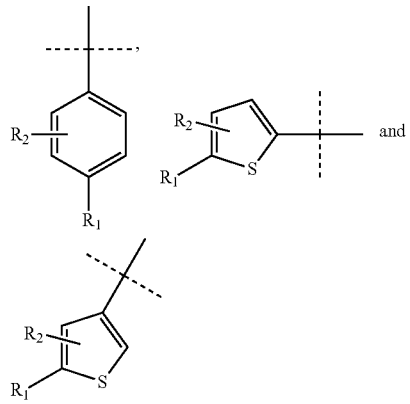

wherein $R_1$ and $R_2$ are as defined previously.

In a further aspect of the invention, $R_1$ is

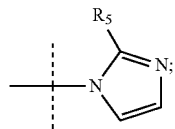

wherein $R_5$ is selected from the group consisting of hydrogen, methyl, and ethyl.

In a further aspect of the invention, $ArR_1R_2$ is selected from the group consisting of: 4-methoxyphenyl, 4-chloro-2-methoxyphenyl, 4-hydroxyphenyl, 4-carbamoylphenyl, and 4-bromophenyl.

In a further aspect of the invention, $R_3$ is selected from the group consisting of hydrogen, methyl, and methoxy.

In a further aspect of the invention, suitable compounds of Formula II include, but are not limited to:

3-(3-(4-carbamoyl-2-methylphenyl)-4-(4-methoxyphenyl)thiophen-2-yl)propanoic acid;

3-(3-(4-carbamoylphenyl)-4-(4-chloro-2-methoxyphenyl)thiophen-2-yl)propanoic acid;

3-(3-(4-chloro-2-methoxyphenyl)-4-(4-hydroxyphenyl)thiophen-2-yl)propanoic acid;

3-(4-(4-chloro-2-methoxyphenyl)-3-(4-hydroxyphenyl)thiophen-2-yl)propanoic acid;

3-(4-(4-chloro-2-methoxyphenyl)-3-(4-(methylsulfonamido)phenyl)thiophen-2-yl)propanoic acid;

3-(4-(4-carbamoylphenyl)-3-(4-(2-methyl-1H-imidazol-1-yl)phenyl)thiophen-2-yl)propanoic acid;

3-(3-(4-carbamoyl-2-methylphenyl)-4-(4-(2-methyl-1H-imidazol-1-yl)phenyl)thiophen-2-yl)propanoic acid;

3-(3-(4-carbamoylphenyl)-4-(4-(2-methyl-1H-imidazol-1-yl)phenyl)thiophen-2-yl)propanoic acid;

3-(4-(4-(2-methyl-1H-imidazol-1-yl)phenyl)-3-(2-methyl-4-(methylsulfonamido)phenyl)thiophen-2-yl)propanoic acid;

3-(4-(4-chloro-2-methoxyphenyl)-3-(2-methyl-4-(methylsulfonamido)phenyl)thiophen-2-yl)propanoic acid;

3-(4-(4-carbamoyl-2-methylphenyl)-5-(2-methyl-1H-imidazol-1-yl)-2,3'-bithiophen-5'-yl)propanoic acid;

3-(5-(2-methyl-1H-imidazol-1-yl)-4'-(2-methyl-4-(methylsulfonamido)phenyl)-2,3'-bithiophen-5'-yl)propanoic acid; and 3-(4-(4-bromophenyl)-3-(4-carbamoyl-2-methylphenyl)thiophen-2-yl)propanoic acid.

In one of its aspects the present invention provides a compound having a structure shown in Formula III, or a pharmaceutically acceptable salt, stereoisomer, prodrug, or metabolite thereof:

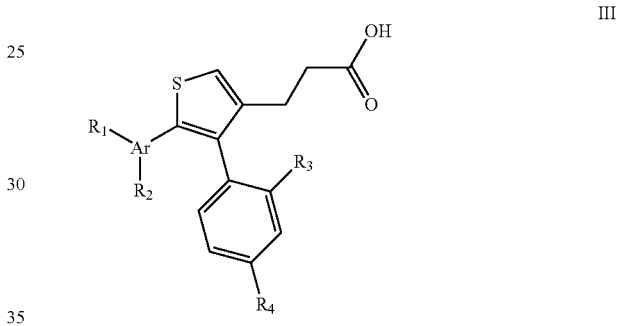

III wherein:

Ar is selected from the group consisting of phenyl and thiophen-yl;

$R_1$ is selected from the group consisting of hydrogen, unsubstituted imidazolyl, substituted imidazolyl, carbamoyl, chloro, bromo, fluoro, hydroxy, and methoxy;

$R_2$ is selected from the group consisting of hydrogen, methyl, chloro, fluoro, hydroxy, methoxy, ethoxy, propoxy, carbamoyl, dimethylamino, amino, formamido, and trifluoromethyl; and $R_3$ is selected from the group consisting of hydrogen, methyl, methoxy, chloro, and fluoro; and $R_4$ is selected from the group consisting of $CONH_2$, $NHSO_2CH_3$, hydroxy, chloro, and substituted and unsubstituted imidazolyl.

In a further aspect of the invention, Ar is selected from the group consisting of

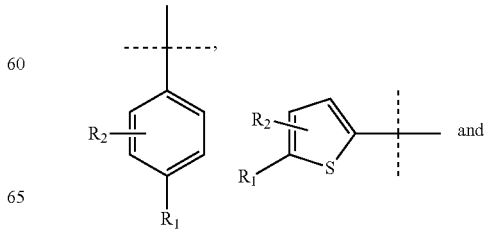

-continued

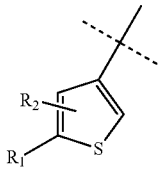

wherein R₁ and R₂ are as defined previously.

In a further aspect of the invention, R₁ is

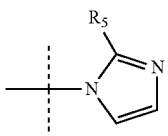

wherein $R_5$ is selected from the group consisting of hydrogen, methyl, and ethyl.

In a further aspect of the invention, ArR₁R₂ is selected from the group consisting of: 4-methoxyphenyl, 4-chloro-2-methoxyphenyl, 4-hydroxyphenyl, 4-carbamoylphenyl, and 4-bromophenyl.

In a further aspect of the invention, $R_3$ is selected from the group consisting of hydrogen, methyl, and methoxy.

In a further aspect of the invention, a suitable compound of Formula III includes, but is not limited to:
3-(4-(4-carbamoyl-2-methylphenyl)-5-(4-methoxyphenyl) thiophen-3-yl)propanoic acid.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such substituent. Combinations of substituents and/or variables are permissible, but only if such combinations result in stable compounds.

The compounds described herein may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic, and geometric isomeric forms of a structure are intended, unless the specific stereochemistry or isomeric form is specifically indicated. All tautomers of shown or described compounds are also considered to be part of the present invention.

It is to be understood that isomers arising from such asymmetry (e.g., all enantiomers and diastereomers) are included within the scope of the invention, unless indicated otherwise. Such isomers can be obtained in substantially pure form by classical separation techniques and by stereochemically controlled synthesis. Furthermore, the structures and other compounds and moieties discussed in this application also include all tautomers thereof. Alkenes can include either the E- or Z-geometry, where appropriate.

2. Representative Compounds

Examples 1-14 list representative novel thiophene analogs of Formula I. The synthetic methods that can be used to prepare each compound are detailed in Examples 1-14, with reference to synthetic schemes depicted before Example 1, and reference to intermediates described in Example 15. Supporting mass spectrometry data and proton NMR data for each compound is also included in Examples 1-14. GSNOR inhibitor activity was determined by the assay described in Example 16 and $IC_{50}$ values were obtained. GSNOR inhibitor compounds in Examples 1-14 had an $IC_{50}$ of about <10 µM. GSNOR inhibitor compounds in Examples 1, 2, 4, 7-9, 11-13, 14 had an $IC_{50}$ of about less than 1.0 µM.

C. Definitions

As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

The term "acyl" includes compounds and moieties that contain the acetyl radical ($CH_3CO$—) or a carbonyl group to which a straight or branched chain lower alkyl residue is attached.

The term "alkyl" as used herein refers to a straight or branched chain, saturated hydrocarbon having the indicated number of carbon atoms. For example, $(C_1-C_6)$alkyl is meant to include, but is not limited to methyl, ethyl, propyl, isopropyl, butyl, sec-butyl, tert-butyl, pentyl, isopentyl, neopentyl, hexyl, isohexyl, and neohexyl. An alkyl group can be unsubstituted or optionally substituted with one or more substituents as described herein.

The term "alkenyl" as used herein refers to a straight or branched chain unsaturated hydrocarbon having the indicated number of carbon atoms and at least one double bond. Examples of a $(C_2-C_8)$alkenyl group include, but are not limited to, ethylene, propylene, 1-butylene, 2-butylene, isobutylene, sec-butylene, 1-pentene, 2-pentene, isopentene, 1-hexene, 2-hexene, 3-hexene, isohexene, 1-heptene, 2-heptene, 3-heptene, isoheptene, 1-octene, 2-octene, 3-octene, 4-octene, and isooctene. An alkenyl group can be unsubstituted or optionally substituted with one or more substituents as described herein.

The term "alkynyl" as used herein refers to a straight or branched chain unsaturated hydrocarbon having the indicated number of carbon atoms and at least one triple bond. Examples of a $(C_2-C_8)$alkynyl group include, but are not limited to, acetylene, propyne, 1-butyne, 2-butyne, 1-pentyne, 2-pentyne, 1-hexyne, 2-hexyne, 3-hexyne, 1-heptyne, 2-heptyne, 3-heptyne, 1-octyne, 2-octyne, 3-octyne, and 4-octyne. An alkynyl group can be unsubstituted or optionally substituted with one or more substituents as described herein.

The term "alkoxy" as used herein refers to an —O-alkyl group having the indicated number of carbon atoms. For example, a $(C_1-C_6)$alkoxy group includes —O-methyl, —O-ethyl, —O-propyl, —O-isopropyl, —O-butyl, —O-sec-butyl, —O-tert-butyl, —O-pentyl, —O-isopentyl, —O-neopentyl, —O-hexyl, —O-isohexyl, and —O-neohexyl.

The term "aminoalkyl" as used herein, refers to an alkyl group (typically one to six carbon atoms) wherein one or more of the $C_1-C_6$ alkyl group's hydrogen atoms is replaced with an amine of formula —N(R^c)₂, wherein each occurrence of R^c is independently —H or $(C_1-C_6)$alkyl. Examples of aminoalkyl groups include, but are not limited to, —$CH_2NH_2$, —$CH_2CH_2NH_2$, —$CH_2CH_2CH_2NH_2$, —CH$_2$CH$_2$CH$_2$CH$_2$NH$_2$, —CH$_2$CH$_2$CH$_2$CH$_2$CH$_2$NH$_2$, —CH$_2$CH$_2$CH$_2$CH$_2$CH$_2$CH$_2$NH$_2$, —CH$_2$CH$_2$CH$_2$N (CH$_3$)$_2$, t-butylaminomethyl, isopropylaminomethyl, and the like.

The term "aryl" as used herein refers to a 5- to 14-membered monocyclic, bicyclic, or tricyclic aromatic ring system. Examples of an aryl group include phenyl and naphthyl. An aryl group can be unsubstituted or optionally substituted with one or more substituents as described herein below. Examples of aryl groups include phenyl or aryl heterocycles such as, pyrrole, furan, thiophene, thiazole, isothiazole, imidazole, triazole, tetrazole, pyrazole, oxazole, isoxazole, pyridine, pyrazine, pyridazine, and pyrimidine, and the like.

As used herein, the term "bioactivity" indicates an effect on one or more cellular or extracellular process (e.g., via binding, signaling, etc.) which can impact physiological or pathophysiological processes.

The term "carbonyl" includes compounds and moieties which contain a carbon connected with a double bond to an oxygen atom. Examples of moieties containing a carbonyl include, but are not limited to, aldehydes, ketones, carboxylic acids, amides, esters, anhydrides, etc.

The term "carboxy" or "carboxyl" means a —COOH group or carboxylic acid.

The term "C$_m$-C$_n$" means "m" number of carbon atoms to "n" number of carbon atoms. For example, the term "C$_1$-C$_6$" means one to six carbon atoms (C$_1$, C$_2$, C$_3$, C$_4$, C$_5$, or C$_6$). The term "C$_2$-C$_6$" includes two to six carbon atoms (C$_2$, C$_3$, C$_4$, C$_5$, or C$_6$). The term "C$_3$-C$_6$" includes three to six carbon atoms (C$_3$, C$_4$, C$_5$, or C$_6$).

The term "cycloalkyl" as used herein refers to a 3- to 14-membered saturated or unsaturated non-aromatic monocyclic, bicyclic, or tricyclic hydrocarbon ring system. Included in this class are cycloalkyl groups which are fused to a benzene ring. Representative cycloalkyl groups include, but are not limited to, cyclopropyl, cyclobutyl, cyclobutenyl, cyclopentyl, cyclopentenyl, cyclopentadienyl, cyclohexyl, cyclohexenyl, 1,3-cyclohexadienyl, cycloheptyl, cycloheptenyl, 1,3-cycloheptadienyl, 1,4-cycloheptadienyl, -1,3,5-cycloheptatrienyl, cyclooctyl, cyclooctenyl, 1,3-cyclooctadienyl, 1,4-cyclooctadienyl, -1,3,5-cyclooctatrienyl, decahydronaphthalene, octahydronaphthalene, hexahydronaphthalene, octahydroindene, hexahydroindene, tetrahydroindene, decahydrobenzocycloheptene, octahydrobenzocycloheptene, hexahydrobenzocycloheptene, tetrahydrobenzocycloheptene, dodecahydroheptalene, decahydroheptalene, octahydroheptalene, hexahydroheptalene, tetrahydroheptalene, (1s,3s)-bicyclo[1.1.0]butane, bicyclo[1.1.1]pentane, bicyclo[2.1.1]hexane, Bicyclo[2.2.1]heptane, bicyclo[2.2.2]octane, bicyclo[3.1.1]heptane, bicyclo[3.2.1]octane, bicyclo[3.3.1]nonane, bicyclo[3.3.2]decane, bicyclo[3.3.]undecane, bicyclo[4.2.2]decane, and bicyclo[4.3.1]decane. A cycloalkyl group can be unsubstituted or optionally substituted with one or more substituents as described herein below.

The term "halogen" includes fluorine, bromine, chlorine, iodine, etc.

The term "haloalkyl," as used herein, refers to a C$_1$-C$_6$ alkyl group wherein from one or more of the C$_1$-C$_6$ alkyl group's hydrogen atom is replaced with a halogen atom, which can be the same or different. Examples of haloalkyl groups include, but are not limited to, trifluoromethyl, 2,2,2-trifluoroethyl, 4-chlorobutyl, 3-bromopropyl, pentachloroethyl, and 1,1,1-trifluoro-2-bromo-2-chloroethyl.

The term "heteroalkyl," by itself or in combination with another term, means, unless otherwise stated, a stable straight or branched chain alkyl, or combinations thereof, consisting of carbon atoms and from one to three heteroatoms selected from the group consisting of O, N, and S, and wherein the nitrogen and sulfur atoms may optionally be oxidized and the nitrogen heteroatom may optionally be quaternized. The heteroatom(s) O, N, and S can be placed at any position of the heteroalkyl group. Examples include —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$—S(O)—CH$_3$, —CH$_2$—CH$_2$—S(O)$_2$—CH$_3$, and —CH$_2$—CH=N—OCH$_3$. Up to two heteroatoms can be consecutive, for example, —CH$_2$—NH—OCH$_3$. When a prefix such as (C$_2$-C$_8$) is used to refer to a heteroalkyl group, the number of carbons (2 to 8, in this example) is meant to include the heteroatoms as well. For example, a C$_2$-heteroalkyl group is meant to include, for example, —CH$_2$OH (one carbon atom and one heteroatom replacing a carbon atom) and —CH$_2$SH.

To further illustrate the definition of a heteroalkyl group, where the heteroatom is oxygen, a heteroalkyl group can be an oxyalkyl group. For instance, (C$_2$-C$_5$)oxyalkyl is meant to include, for example —CH$_2$—O—CH$_3$ (a C$_3$-oxyalkyl group with two carbon atoms and one oxygen replacing a carbon atom), —CH$_2$CH$_2$CH$_2$CH$_2$OH, —OCH$_2$CH$_2$OCH$_2$CH$_2$OH, —OCH$_2$CH(OH)CH$_2$OH, and the like.

The term "heteroaryl" as used herein refers to an aromatic heterocycle ring of 5 to 14 members and having at least one heteroatom selected from nitrogen, oxygen, and sulfur, and containing at least 1 carbon atom, including monocyclic, bicyclic, and tricyclic ring systems. Representative heteroaryls are triazolyl, tetrazolyl, oxadiazolyl, pyridyl, furyl, benzofuranyl, thienyl, benzothienyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, quinazolinyl, pyrimidyl, azepinyl, oxepinyl, quinoxalinyl and oxazolyl. A heteroaryl group can be unsubstituted or optionally substituted with one or more substituents as described herein below.

As used herein, the term "heteroatom" is meant to include oxygen (O), nitrogen (N), and sulfur (S).

As used herein, the term "heterocycle" refers to 3- to 14-membered ring systems which are either saturated, unsaturated, or aromatic, and which contains from 1 to 4 heteroatoms independently selected from nitrogen, oxygen, and sulfur, and wherein the nitrogen and sulfur heteroatoms can be optionally oxidized, and the nitrogen heteroatom can be optionally quaternized, including, including monocyclic, bicyclic, and tricyclic ring systems. The bicyclic and tricyclic ring systems may encompass a heterocycle or heteroaryl fused to a benzene ring. The heterocycle can be attached via any heteroatom or carbon atom, where chemically acceptable. Heterocycles include heteroaryls as defined above. Representative examples of heterocycles include, but are not limited to, aziridinyl, oxiranyl, thiiranyl, triazolyl, tetrazolyl, azirinyl, diaziridinyl, diazirinyl, oxaziridinyl, azetidinyl, azetidinonyl, oxetanyl, thietanyl, piperidinyl, piperazinyl, morpholinyl, pyrrolyl, oxazinyl, thiazinyl, diazinyl, dioxanyl, triazinyl, tetrazinyl, imidazolyl, tetrazolyl, pyrrolidinyl, isoxazolyl, furanyl, furazanyl, pyridinyl, oxazolyl, benzoxazolyl, benzisoxazolyl, thiazolyl, benzthiazolyl, thienyl, pyrazolyl, triazolyl, pyrimidinyl, benzimidazolyl, isoindolyl, indazolyl, benzodiazolyl, benzotriazolyl, benzoxazolyl, benzisoxazolyl, purinyl, indolyl, isoquinolinyl, quinolinyl, and quinazolinyl. A heterocycle group can be unsubstituted or optionally substituted with one or more substituents as described herein below.

The term "heterocycloalkyl," by itself or in combination with other terms, represents, unless otherwise stated, cyclic versions of "heteroalkyl." Additionally, a heteroatom can occupy the position at which the heterocycle is attached to the remainder of the molecule. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The term "hydroxyalkyl," as used herein, refers to an alkyl group having the indicated number of carbon atoms wherein one or more of the hydrogen atoms in the alkyl group is replaced with an —OH group. Examples of hydroxyalkyl groups include, but are not limited to, —CH$_2$OH, —CH$_2$CH$_2$OH, —CH$_2$CH$_2$CH$_2$OH, —CH$_2$CH$_2$CH$_2$CH$_2$OH, —CH$_2$CH$_2$CH$_2$CH$_2$CH$_2$OH, —CH$_2$CH$_2$CH$_2$CH$_2$CH$_2$CH$_2$OH, and branched versions thereof.

The term "hydroxy" or "hydroxyl" includes groups with an —OH or —O$^-$.

As used herein, N-oxide, or amine oxide, refers to a compound derived from a tertiary amine by the attachment of one oxygen atom to the nitrogen atom, $R_3N^+$—$O^-$. By extension the term includes the analogous derivatives of primary and secondary amines.

As used herein and unless otherwise indicated, the term "stereoisomer" means one stereoisomer of a compound that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. In some embodiments, a stereomerically pure compound comprises greater than about 80% by weight of one stereoisomer of the compound and less than about 20% by weight of other stereoisomers of the compound, for example greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound.

As used herein, "protein" is used synonymously with "peptide," "polypeptide," or "peptide fragment". A "purified" polypeptide, protein, peptide, or peptide fragment is substantially free of cellular material or other contaminating proteins from the cell, tissue, or cell-free source from which the amino acid sequence is obtained, or substantially free from chemical precursors or other chemicals when chemically synthesized.

As used herein, "modulate" is meant to refer to an increase or decrease in the levels of a peptide or a polypeptide, or to increase or decrease the stability or activity of a peptide or a polypeptide. The term "inhibit" is meant to refer to a decrease in the levels of a peptide or a polypeptide or to a decrease in the stability or activity of a peptide or a polypeptide. In preferred embodiments, the peptide which is modulated or inhibited is S-nitrosoglutathione (GSNO) or protein S-nitrosothiols (SNOs).

As used here, the terms "nitric oxide" and "NO" encompass uncharged nitric oxide and charged nitric oxide species, particularly including nitrosonium ion (NO$^+$) and nitroxyl ion (NO$^-$). The reactive form of nitric oxide can be provided by gaseous nitric oxide. Compounds having the structure X—NO$_y$, wherein X is a nitric oxide releasing, delivering, or transferring moiety, including any and all such compounds which provide nitric oxide to its intended site of action in a form active for their intended purpose, and Y is 1 or 2.

As utilized herein, the term "pharmaceutically acceptable" means approved by a regulatory agency of a federal or a state government or listed in the U.S. Pharmacopoeia or other generally recognized pharmacopoeia for use in animals and, more particularly, in humans. The term "carrier" refers to a diluent, adjuvant, excipient, or vehicle with which the therapeutic is administered and includes, but is not limited to such sterile liquids as water and oils.

A "pharmaceutically acceptable salt" or "salt" of a compound of the invention is a product of the disclosed compound that contains an ionic bond, and is typically produced by reacting the disclosed compound with either an acid or a base, suitable for administering to a subject. A pharmaceutically acceptable salt can include, but is not limited to, acid addition salts including hydrochlorides, hydrobromides, phosphates, sulphates, hydrogen sulphates, alkylsulphonates, arylsulphonates, arylalkylsulfonates, acetates, benzoates, citrates, maleates, fumarates, succinates, lactates, and tartrates; alkali metal cations such as Li, Na, and K, alkali earth metal salts such as Mg or Ca, or organic amine salts.

A "pharmaceutical composition" is a formulation comprising the disclosed compounds in a form suitable for administration to a subject. A pharmaceutical composition of the invention is preferably formulated to be compatible with its intended route of administration. Examples of routes of administration include, but are not limited to, oral and parenteral, e.g., intravenous, intradermal, subcutaneous, inhalation, topical, transdermal, transmucosal, and rectal administration.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Ring double bonds, as used herein, are double bonds that are formed between two adjacent ring atoms (e.g., C=C, C=N, or N=N).

Substituents for the groups referred to as alkyl, heteroalkyl, alkylene, alkenyl, alkynyl, cycloalkyl, heterocycloalkyl, cycloalkenyl, and heterocycloalkenyl can be selected from a variety of groups including —OR$^{a\prime}$, =O, =NR$^{a\prime}$, =N—OR$^{a\prime}$, —NR$^{a\prime}$R$^{a\prime\prime}$, —SR$^{a\prime}$, -halo, —SiR$^{a\prime}$R$^{a\prime\prime}$R$^{a\prime\prime\prime}$, —OC(O)R$^{a\prime}$, —C(O)R$^{a\prime}$, —CO$_2$R$^{a\prime}$, —CONR$^{a\prime}$R$^{a\prime\prime}$, —OC(O)NR$^{a\prime}$R$^{a\prime\prime}$, —NR$^{a\prime\prime}$C(O)R$^{a\prime}$, —NR$^{a\prime\prime}$C(O)NR$^{a\prime}$R$^{a\prime\prime}$, —NR$^{a\prime\prime\prime}$SO$_2$NR$^{a\prime}$R$^{a\prime\prime}$, —NR$^{a\prime\prime}$CO$_2$R$^{a\prime}$, —NHC(NH$_2$)=NH, —NR$^{a\prime}$C(NH$_2$)=NH, —NHC(NH$_2$)=NR$^{a\prime}$, —S(O)R$^{a\prime}$, —SO$_2$R$^{a\prime}$, —SO$_2$NR$^{a\prime}$R$^{a\prime\prime}$, NR$^{a\prime\prime}$SO$_2$R$^{a\prime\prime}$, —CN, and —NO$_2$, in a number ranging from zero to three, with those groups having zero, one or two substituents being exemplary.

R$^{a\prime}$, R$^{a\prime\prime}$, and R$^{a\prime\prime\prime}$ each independently refer to hydrogen, unsubstituted (C$_1$-C$_8$)alkyl, unsubstituted hetero(C$_1$-C$_8$)alkyl, unsubstituted aryl, and aryl substituted with one to three substituents selected from -halo, unsubstituted alkyl, unsubstituted alkoxy, unsubstituted thioalkoxy, and unsubstituted aryl (C$_1$-C$_4$)alkyl. When R$^{a\prime}$ and R$^{a\prime\prime}$ are attached to the same nitrogen atom, they can be combined with the nitrogen atom to form a 5-, 6-, or 7-membered ring. For example, —NR$^{a\prime}$R$^{a\prime\prime}$ can represent 1-pyrrolidinyl or 4-morpholinyl.

Typically, an alkyl or heteroalkyl group will have from zero to three substituents, with those groups having two or fewer substituents being exemplary of the present invention. An alkyl or heteroalkyl radical can be unsubstituted or monosubstituted. In some embodiments, an alkyl or heteroalkyl radical will be unsubstituted.

Exemplary substituents for the alkyl and heteroalkyl radicals include, but are not limited to —$OR^d$, =O, =$NR^{d"}$, =N—$OR^d$, —$NR^{d'}R^{d"}$, —$SR^{d'}$, -halo, —$SiR^{d'}R^{d"}R^{d"'}$, —OC(O)$R^{d'}$, —C(O)$R^{d'}$, —$CO_2R^{d'}$, —CONR$^{d'}R^{d"}$, —OC(O)NR$^{d'}R^{d"}$, —NR$^{d"}$C(O)$R^{d'}$, —NR$^{d"'}$C(O)NR$^{d'}R^{d"}$, —NR$^{d"'}SO_2NR^{d'}R^{d"}$, —NR$^{d"}CO_2R^{d'}$, —NHC(NH$_2$)=NH, —NR$^{a"}C(NH_2)$=NH, —NHC(NH$_2$)=NR$^{d'}$, —S(O)$R^{d'}$, —$SO_2R^{d'}$, —$SO_2NR^{d'}R^{d"}$, —NR$^{d"}SO_2R^{d'}$, —CN, and —$NO_2$, where $R^{d'}$, $R^{d"}$, and $R^{d"'}$ are as defined above. Typical substituents can be selected from: —$OR^{d'}$, =O, —$NR^{d'}R^{d"}$, -halo, —OC(O)$R^{d'}$, —$CO_2R^{d'}$, —C(O)NR$^{d'}R^{d"}$, —OC(O)NR$^{d'}R^{d"}$, —NR$^{d"}C(O)R^{d'}$, —NR$^{d"}CO_2R^{d'}$, —NR$^{d"'}SO_2NR^{d'}R^{d"}$, —$SO_2R^{d'}$, —$SO_2NR^{d'}R^{d"}$, —NR$^{d"}SO_2R^{d'}$, —CN, and —$NO_2$.

Similarly, substituents for the aryl and heteroaryl groups are varied and selected from: -halo, —$OR^{e'}$, —OC(O)$R^{e'}$, —NR$^{e'}R^{e"}$, —$SR^{e'}$, —$R^{e'}$, —CN, —$NO_2$, —$CO_2R^{e'}$, —C(O)NR$^{e'}R^{e"}$, —C(O)$R^{e'}$, —OC(O)NR$^{e'}R^{e"}$, —NR$^{e"}C(O)R^{e'}$, —NR$^{e"}CO_2R^{e'}$, —NR$^{e"}C(O)NR^{e'}R^{e"}$, —NR$^{e""}SO_2NR^{e'}R^{e"}$, —NHC(NH$_2$)=NH, —NR$^{e"}C(NH_2)$=NH, —NH—C(NH$_2$)=NR$^{e"}$, —S(O)$R^{e'}$, —$SO_2R^{e'}$, —$SO_2NR^{e'}R^{e"}$, —NR$^{e"}SO_2R^{e'}$, —$N_3$, —CH(Ph)$_2$, perfluoroalkoxy, and perfluoro($C_1$-$C_4$)alkyl, in a number ranging from zero to the total number of open valences on the aromatic ring system.

$R^{e'}$, $R^{e"}$ and $R^{e"'}$ are independently selected from hydrogen, unsubstituted ($C_1$-$C_8$)alkyl, unsubstituted hetero($C_1$-$C_8$)alkyl, unsubstituted aryl, unsubstituted heteroaryl, unsubstituted aryl($C_1$-$C_4$)alkyl, and unsubstituted aryloxy($C_1$-$C_4$)alkyl. Typically, an aryl or heteroaryl group will have from zero to three substituents, with those groups having two or fewer substituents being exemplary in the present invention. In one embodiment of the invention, an aryl or heteroaryl group will be unsubstituted or monosubstituted. In another embodiment, an aryl or heteroaryl group will be unsubstituted.

Two of the substituents on adjacent atoms of an aryl or heteroaryl ring in an aryl or heteroaryl group as described herein may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -J-(CH$_2$)$_r$—K—, wherein J and K are independently —CH$_2$—, —O—, —NH—, —S—, —S(O)—, —S(O)$_2$—, —S(O)$_2$NR$^{fi}$—, or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR$^{fi}$—, —S—, —S(O)—, —S(O)$_2$—, or —S(O)$_2$NR$^{a"}$—. The substituent R$^{fi}$ in —NR$^{fi}$— and —S(O)$_2$NR$^{fi}$— is selected from hydrogen or unsubstituted ($C_1$-$C_6$)alkyl.

"Stable compound" and "stable structure" are meant to indicate a compound that is sufficiently robust to survive isolation to a useful degree of purity from a reaction mixture, and formulation into an efficacious therapeutic agent.

As used herein the term "therapeutically effective amount" generally means the amount necessary to ameliorate at least one symptom of a disorder to be prevented, reduced, or treated as described herein. The phrase "therapeutically effective amount" as it relates to the GSNOR inhibitors of the present invention shall mean the GSNOR inhibitor dosage that provides the specific pharmacological response for which the GSNOR inhibitor is administered in a significant number of subjects in need of such treatment. It is emphasized that a therapeutically effective amount of a GSNOR inhibitor that is administered to a particular subject in a particular instance will not always be effective in treating the conditions/diseases described herein, even though such dosage is deemed to be a therapeutically effective amount by those of skill in the art.

The term "biological sample" includes, but is not limited to, samples of blood (e.g., serum, plasma, or whole blood), urine, saliva, sweat, breast milk, vaginal secretions, semen, hair follicles, skin, teeth, bones, nails, or other secretions, body fluids, tissues, or cells. In accordance with the invention, the levels of the GSNOR in the biological sample can be determined by the methods described in U.S. Patent Application Publication No. 2005/0014697.

D. Pharmaceutical Compositions

The invention encompasses pharmaceutical compositions comprising at least one compound of the invention described herein and at least one pharmaceutically acceptable carrier. Suitable carriers are described in "Remington: The Science and Practice, Twentieth Edition," published by Lippincott Williams & Wilkins, which is incorporated herein by reference. Pharmaceutical compositions according to the invention may also comprise one or more non-inventive compound active agents.

The pharmaceutical compositions of the invention can comprise novel compounds described herein, the pharmaceutical compositions can comprise known compounds which previously were not known to have GSNOR inhibitor activity, or a combination thereof.

The compounds of the invention can be utilized in any pharmaceutically acceptable dosage form, including, but not limited to injectable dosage forms, liquid dispersions, gels, aerosols, ointments, creams, lyophilized formulations, dry powders, tablets, capsules, controlled release formulations, fast melt formulations, delayed release formulations, extended release formulations, pulsatile release formulations, mixed immediate release and controlled release formulations, etc. Specifically, the compounds of the invention described herein can be formulated: (a) for administration selected from the group consisting of oral, pulmonary, intravenous, intra-arterial, intrathecal, intra-articular, rectal, ophthalmic, colonic, parenteral, intracisternal, intravaginal, intraperitoneal, local, buccal, nasal, and topical administration; (b) into a dosage form selected from the group consisting of liquid dispersions, gels, aerosols, ointments, creams, tablets, sachets, and capsules; (c) into a dosage form selected from the group consisting of lyophilized formulations, dry powders, fast melt formulations, controlled release formulations, delayed release formulations, extended release formulations, pulsatile release formulations, and mixed immediate release and controlled release formulations; or (d) any combination thereof.

For respiratory infections, an inhalation formulation can be used to achieve high local concentrations. Formulations suitable for inhalation include dry power or aerosolized or vaporized solutions, dispersions, or suspensions capable of being dispensed by an inhaler or nebulizer into the endobronchial or nasal cavity of infected patients to treat upper and lower respiratory bacterial infections.

Solutions or suspensions used for parenteral, intradermal, or subcutaneous application can comprise one or more of the following components: (1) a sterile diluent such as water for injection, saline solution, fixed oils, polyethylene glycols, glycerine, propylene glycol, or other synthetic solvents; (2) antibacterial agents such as benzyl alcohol or methyl parabens; (3) antioxidants such as ascorbic acid or sodium bisulfite; (4) chelating agents such as ethylenediaminetetraacetic acid; (5) buffers such as acetates, citrates, or phosphates; and (5) agents for the adjustment of tonicity such as sodium chloride or dextrose. The pH can be adjusted with acids or bases, such as hydrochloric acid or sodium hydroxide. A parenteral preparation can be enclosed in ampoules, disposable syringes, or multiple dose vials made of glass or plastic.

Pharmaceutical compositions suitable for injectable use may comprise sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL (BASF, Parsippany, N.J.), or phosphate buffered saline (PBS). In all cases, the composition must be sterile and should be fluid to the extent that easy syringability exists. The pharmaceutical composition should be stable under the conditions of manufacture and storage and should be preserved against the contaminating action of microorganisms such as bacteria and fungi.

The carrier can be a solvent or dispersion medium comprising, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion, and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol or sorbitol, and inorganic salts such as sodium chloride in the composition. Prolonged absorption of the injectable compositions can be brought about by including in the composition an agent which delays absorption, for example, aluminum monostearate and gelatin.

Sterile injectable solutions can be prepared by incorporating the active reagent in the required amount in an appropriate solvent with one or a combination of ingredients enumerated above, as required, followed by filtered sterilization. Generally, dispersions are prepared by incorporating at least one compound of the invention into a sterile vehicle that contains a basic dispersion medium and any other required ingredients. In the case of sterile powders for the preparation of sterile injectable solutions, exemplary methods of preparation include vacuum drying and freeze-drying, both of which yield a powder of a compound of the invention plus any additional desired ingredient from a previously sterile-filtered solution thereof.

Oral compositions generally include an inert diluent or an edible carrier. They can be enclosed, for example, in gelatin capsules or compressed into tablets. For the purpose of oral therapeutic administration, the compound of the invention can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition.

For administration by inhalation, the compounds are delivered in the form of an aerosol spray from pressured container or dispenser that contains a suitable propellant, e.g., a gas such as carbon dioxide, a nebulized liquid, or a dry powder from a suitable device. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active reagents are formulated into ointments, salves, gels, or creams as generally known in the art. The reagents can also be prepared in the form of suppositories (e.g., with conventional suppository bases such as cocoa butter and other glycerides) or retention enemas for rectal delivery.

In one embodiment, the compounds of the invention are prepared with carriers that will protect against rapid elimination from the body. For example, a controlled release formulation can be used, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Additionally, suspensions of the compounds of the invention may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also include suitable stabilizers or agents to increase the solubility of the compounds and allow for the preparation of highly concentrated solutions.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of the compound of the invention calculated to produce the desired therapeutic effect in association with the required pharmaceutical carrier. The specification for the dosage unit forms of the invention are dictated by and directly dependent on the unique characteristics of the compound of the invention and the particular therapeutic effect to be achieved, and the limitations inherent in the art of compounding such an active agent for the treatment of individuals.

Pharmaceutical compositions according to the invention comprising at least one compound of the invention can comprise one or more pharmaceutical excipients. Examples of such excipients include, but are not limited to binding agents, filling agents, lubricating agents, suspending agents, sweeteners, flavoring agents, preservatives, buffers, wetting agents, disintegrants, effervescent agents, and other excipients. Such excipients are known in the art. Exemplary excipients include: (1) binding agents which include various celluloses and cross-linked polyvinylpyrrolidone, microcrystalline cellulose, such as Avicel® PH101 and Avicel® PH102, silicified microcrystalline cellulose (ProSolv SMCC™), gum tragacanth and gelatin; (2) filling agents such as various starches, lactose, lactose monohydrate, and lactose anhydrous; (3) disintegrating agents such as alginic acid, Primogel, corn starch, lightly crosslinked polyvinyl pyrrolidone, potato starch, maize starch, and modified starches, croscarmellose sodium, cross-povidone, sodium starch glycolate, and mixtures thereof; (4) lubricants, including agents that act on the flowability of a powder to be compressed, include magnesium stearate, colloidal silicon dioxide, such as Aerosil® 200, talc, stearic acid, calcium stearate, and silica gel; (5) glidants such as colloidal silicon dioxide; (6) preservatives, such as potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chloride; (7) diluents such as pharmaceutically acceptable inert fillers, such as microcrystalline cellulose, lactose, dibasic calcium phosphate, saccharides, and/or mixtures of any of the foregoing; examples of diluents include microcrystalline cellulose, such as Avicel® PH101 and Avicel® PH102; lactose such as lactose monohydrate, lactose anhydrous, and Pharmatose® DCL21; dibasic calcium phosphate such as Emcompress®; mannitol; starch; sorbitol; sucrose; and glucose; (8) sweetening agents, including any natural or artificial sweetener, such as sucrose, saccharin sucrose, xylitol, sodium saccharin, cyclamate, aspartame, and acesulfame; (9) flavoring agents, such as peppermint, methyl salicylate, orange flavoring, Magnasweet® (trademark of MAFCO), bubble gum flavor, fruit flavors, and the like; and (10) effervescent agents, including effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

E. Kits Comprising the Compositions of the Invention

The present invention also encompasses kits comprising the compositions of the invention. Such kits can comprise, for example, (1) at least one compound of the invention; and (2) at least one pharmaceutically acceptable carrier, such as a solvent or solution. Additional kit components can optionally include, for example: (1) any of the pharmaceutically acceptable excipients identified herein, such as stabilizers, buffers, etc., (2) at least one container, vial, or similar apparatus for holding and/or mixing the kit components; and (3) delivery apparatus, such as an inhaler, nebulizer, syringe, etc.

F. Methods of Preparing Compounds of the Invention

The compounds of the invention can readily be synthesized using known synthetic methodologies or via a modification of known synthetic methodologies. As would be readily recognized by a skilled artisan, the methodologies described below allow the synthesis of thiophenes having a variety of substituents. Exemplary synthetic methods are described in the examples below.

If needed, further purification and separation of enantiomers and diastereomers can be achieved by routine procedures known in the art. Thus, for example, the separation of enantiomers of a compound can be achieved by the use of chiral HPLC and related chromatographic techniques. Diastereomers can be similarly separated. In some instances, however, diastereomers can simply be separated physically, such as, for example, by controlled precipitation or crystallization.

The process of the invention, when carried out as prescribed herein, can be conveniently performed at temperatures that are routinely accessible in the art. In one embodiment, the process is performed at a temperature in the range of about 25° C. to about 110° C. In another embodiment, the temperature is in the range of about 40° C. to about 100° C. In yet another embodiment, the temperature is in the range of about 50° C. to about 95° C.

Synthetic steps that require a base are carried out using any convenient organic or inorganic base. Typically, the base is not nucleophilic. Thus, in one embodiment, the base is selected from carbonates, phosphates, hydroxides, alkoxides, salts of disilazanes, and tertiary amines.

The process of the invention, when performed as described herein, can be substantially complete after several minutes to after several hours depending upon the nature and quantity of reactants and reaction temperature. The determination of when the reaction is substantially complete can be conveniently evaluated by ordinary techniques known in the art such as, for example, HPLC, LCMS, TLC, and $^1$H NMR.

G. Methods of Treatment

The invention encompasses methods of preventing or treating (e.g., alleviating one or more symptoms of) medical conditions through use of one or more of the disclosed compounds. The methods comprise administering a therapeutically effective amount of a compound of the invention to a patient in need. The compositions of the invention can also be used for prophylactic therapy.

The compound of the invention used in the methods of treatment according to the invention can be: (1) a novel compound described herein, or a pharmaceutically acceptable salt thereof, a stereoisomer thereof, a prodrug thereof, or a metabolite thereof; (2) a compound which was known prior to the present invention, but wherein it was not known that the compound is a GSNOR inhibitor, or a pharmaceutically acceptable salt thereof, a prodrug thereof, or a metabolite thereof; or (3) a compound which was known prior to the present invention, and wherein it was known that the compound is a GSNOR inhibitor, but wherein it was not known that the compound is useful for the methods of treatment described herein, or a pharmaceutically acceptable salt thereof, a prodrug thereof, or a metabolite thereof.

The patient can be any animal, domestic, livestock, or wild, including, but not limited to cats, dogs, horses, pigs, and cattle, and preferably human patients. As used herein, the terms patient and subject may be used interchangeably.

As used herein, "treating" describes the management and care of a patient for the purpose of combating a disease, condition, or disorder and includes the administration of a compound of the present invention to prevent the onset of the symptoms or complications, alleviating the symptoms or complications, or eliminating the disease, condition, or disorder. More specifically, "treating" includes reversing, attenuating, alleviating, minimizing, suppressing, or halting at least one deleterious symptom or effect of a disease (disorder) state, disease progression, disease causative agent (e.g., bacteria or viruses), or other abnormal condition. Treatment is continued as long as symptoms and/or pathology ameliorate.

In general, the dosage, i.e., the therapeutically effective amount, ranges from 1 µg/kg to 10 g/kg and often ranges from 10 µg/kg to 1 g/kg or 10 µg/kg to 100 mg/kg body weight of the subject being treated, per day.

H. GSNOR Uses

In subjects with deleteriously high levels of GSNOR or GSNOR activity, modulation may be achieved, for example, by administering one or more of the disclosed compounds that disrupts or down-regulates GSNOR function, or decreases GSNOR levels. These compounds may be administered with other GSNOR inhibitor agents, such as anti-GSNOR antibodies or antibody fragments, GSNOR antisense, iRNA, or small molecules, or other inhibitors, alone or in combination with other agents as described in detail herein.

The present invention provides a method of treating a subject afflicted with a disorder ameliorated by NO donor therapy. Such a method comprises administering to a subject a therapeutically effective amount of a GSNOR inhibitor.

The disorders can include pulmonary disorders associated with hypoxemia and/or smooth muscle constriction in the lungs and airways and/or lung infection and/or lung inflammation and/or lung injury (e.g., pulmonary hypertension, ARDS, asthma, pneumonia, pulmonary fibrosis/interstitial lung diseases, cystic fibrosis, COPD); cardiovascular disease and heart disease (e.g., hypertension, ischemic coronary syndromes, atherosclerosis, heart failure, glaucoma); diseases characterized by angiogenesis (e.g., coronary artery disease); disorders where there is risk of thrombosis occurring; disorders where there is risk of restenosis occurring; inflammatory diseases (e.g., AIDS related dementia, inflammatory bowel disease (IBD), Crohn's disease, colitis, and psoriasis); functional bowel disorders (e.g., irritable bowel syndrome (IBS)); diseases where there is risk of apoptosis occurring (e.g., heart failure, atherosclerosis, degenerative neurologic disorders, arthritis, and liver injury (ischemic or alcoholic)); impotence; sleep apnea; diabetic wound healing; cutaneous infections; treatment of psoriasis; obesity caused by eating in response to craving for food; stroke; reperfusion injury (e.g., traumatic muscle injury in heart or lung or crush injury); and disorders where preconditioning of heart or brain for NO protection against subsequent ischemic events is beneficial, central nervous system (CNS) disorders (e.g., anxiety, depression, psychosis, and schizophrenia); and infections caused by bacteria (e.g., tuberculosis, C. difficile infections, among others).

In one embodiment, the compounds of the present invention or a pharmaceutically acceptable salt thereof, or a prodrug or metabolite thereof, can be administered in combination with an NO donor. An NO donor donates nitric oxide or a related redox species and more generally provides nitric oxide bioactivity, that is activity which is identified with nitric oxide, e.g., vasorelaxation or stimulation or inhibition of a receptor protein, e.g., ras protein, adrenergic receptor, NFκB. NO donors including S-nitroso, O-nitroso, C-nitroso, and N-nitroso compounds and nitro derivatives thereof and metal NO complexes, but not excluding other NO bioactivity generating compounds, useful herein are described in "Methods in Nitric Oxide Research," Feelisch et al. eds., pages 71-115 (J. S., John Wiley & Sons, New York, 1996), which is incorporated herein by reference. NO donors which are C-nitroso compounds where nitroso is attached to a tertiary carbon which are useful herein include those described in U.S. Pat. No. 6,359,182 and in WO 02/34705. Examples of S-nitroso compounds, including S-nitrosothiols useful herein, include, for example, S-nitrosoglutathione, S-nitroso-N-acetylpenicillamine, S-nitroso-cysteine and ethyl ester thereof, S-nitroso cysteinyl glycine, S-nitroso-gamma-methyl-L-homocysteine, S-nitroso-L-homocysteine, S-nitroso-gamma-thio-L-leucine, S-nitroso-delta-thio-L-leucine, and S-nitrosoalbumin. Examples of other NO donors useful herein are sodium nitroprusside (nipride), ethyl nitrite, isosorbide, nitroglycerin, SIN 1 which is molsidomine, furoxamines, N-hydroxy(N-nitrosamine), and perfluorocarbons that have been saturated with NO or a hydrophobic NO donor.

The combination of a GSNOR inhibitor with R(+) enantiomer of amlodipine, a known NO releaser (Zhang at al., *J. Cardiovasc. Pharm.* 39: 208-214 (2002)) is also an embodiment of the present invention.

The present invention also provides a method of treating a subject afflicted with pathologically proliferating cells where the method comprises administering to said subject a therapeutically effective amount of an inhibitor of GSNOR. The inhibitors of GSNOR are the compounds as defined above, or a pharmaceutically acceptable salt thereof, or a prodrug or metabolite thereof, in combination with a pharmaceutically acceptable carrier. Treatment is continued as long as symptoms and/or pathology ameliorate.

In another embodiment, the pathologically proliferating cells can be pathologically proliferating microbes. The microbes involved can be those where GSNOR is expressed to protect the microbe from nitrosative stress or where a host cell infected with the microbe expresses the enzyme, thereby protecting the microbe from nitrosative stress. The term "pathologically proliferating microbes" is used herein to mean pathologic microorganisms including, but not limited to, pathologic bacteria, pathologic viruses, pathologic *Chlamydia*, pathologic protozoa, pathologic *Rickettsia*, pathologic fungi, and pathologic mycoplasmata. More detail on the applicable microbes is set forth at columns 11 and 12 of U.S. Pat. No. 6,057,367. The term "host cells infected with pathologic microbes" includes not only mammalian cells infected with pathologic viruses but also mammalian cells containing intracellular bacteria or protozoa, e.g., macrophages containing *Mycobacterium tuberculosis, Mycobacterium leper* (leprosy), or *Salmonella typhi* (typhoid fever).

In another embodiment, the pathologically proliferating cells can be pathologic helminths. The term "pathologic helminths" is used herein to refer to pathologic nematodes, pathologic trematodes and pathologic cestodes. More detail on the applicable helminths is set forth at column 12 of U.S. Pat. No. 6,057,367.

In another embodiment, the pathologically proliferating cells can be pathologically proliferating mammalian cells. The term "pathologically proliferating mammalian cells" as used herein means cells of the mammal that grow in size or number in said mammal so as to cause a deleterious effect in the mammal or its organs. The term includes, for example, the pathologically proliferating or enlarging cells causing restenosis, the pathologically proliferating or enlarging cells causing benign prostatic hypertrophy, the pathologically proliferating cells causing myocardial hypertrophy, and proliferating cells at inflammatory sites such as synovial cells in arthritis or cells associated with a cell proliferation disorder.

As used herein, the term "cell proliferative disorder" refers to conditions in which the unregulated and/or abnormal growth of cells can lead to the development of an unwanted condition or disease, which can be cancerous or non-cancerous, for example a psoriatic condition. As used herein, the term "psoriatic condition" refers to disorders involving keratinocyte hyperproliferation, inflammatory cell infiltration, and cytokine alteration. The cell proliferative disorder can be a precancerous condition or cancer. The cancer can be primary cancer or metastatic cancer, or both.

As used herein, the term "cancer" includes solid tumors, such as lung, breast, colon, ovarian, pancreas, prostate, adenocarcinoma, squamous carcinoma, sarcoma, malignant glioma, leiomyosarcoma, hepatoma, head and neck cancer, malignant melanoma, non-melanoma skin cancers, as well as hematologic tumors and/or malignancies, such as leukemia, childhood leukemia and lymphomas, multiple myeloma, Hodgkin's disease, lymphomas of lymphocytic and cutaneous origin, acute and chronic leukemia such as acute lymphoblastic, acute myelocytic, or chronic myelocytic leukemia, plasma cell neoplasm, lymphoid neoplasm, and cancers associated with AIDS.

In addition to psoriatic conditions, the types of proliferative diseases which may be treated using the compositions of the present invention are epidermic and dermoid cysts, lipomas, adenomas, capillary and cutaneous hemangiomas, lymphangiomas, nevi lesions, teratomas, nephromas, myofibromatosis, osteoplastic tumors, and other dysplastic masses, and the like. In one embodiment, proliferative diseases include dysplasias and disorders of the like.

In one embodiment, treating cancer comprises a reduction in tumor size, decrease in tumor number, a delay of tumor growth, decrease in metastaic lesions in other tissues or organs distant from the primary tumor site, an improvement in the survival of patients, or an improvement in the quality of patient life, or at least two of the above.

In another embodiment, treating a cell proliferative disorder comprises a reduction in the rate of cellular proliferation, reduction in the proportion of proliferating cells, a decrease in size of an area or zone of cellular proliferation, or a decrease in the number or proportion of cells having an abnormal appearance or morphology, or at least two of the above.

In yet another embodiment, the compounds of the present invention or a pharmaceutically acceptable salt thereof, a prodrug thereof, or metabolite thereof can be administered in combination with a second chemotherapeutic agent. In a further embodiment, the second chemotherapeutic agent is selected from the group consisting of tamoxifen, raloxifene, anastrozole, exemestane, letrozole, cisplatin, carboplatin, paclitaxel, cyclophosphamide, lovastatin, minosine, gemcitabine, araC, 5-fluorouracil, methotrexate, docetaxel, goserelin, vincristin, vinblastin, nocodazole, teniposide, etoposide, epothilone, navelbine, camptothecin, daunonibicin, dactinomycin, mitoxantrone, amsacrine, doxorubicin, epirubicin, idarubicin imatanib, gefitinib, erlotinib, sorafenib, sunitinib malate, trastuzumab, rituximab, cetuximab, and bevacizumab.

In one embodiment, the compounds of the present invention or a pharmaceutically acceptable salt thereof, a prodrug thereof, a metabolite thereof can be administered in combination with an agent that imposes nitrosative or oxidative stress. Agents for selectively imposing nitrosative stress to inhibit proliferation of pathologically proliferating cells in combination therapy with GSNOR inhibitors herein and dosages and routes of administration therefor include those disclosed in U.S. Pat. No. 6,057,367, which is incorporated herein. Supplemental agents for imposing oxidative stress (i.e., agents that increase GSSG (oxidized glutathione) over GSH (glutathione) ratio or NAD(P) over NAD(P)H ratio or increase thiobarbituric acid derivatives) in combination therapy with GSNOR inhibitors herein include, for example, L-buthionine-S-sulfoximine (BSO), glutathione reductase inhibitors (e.g., BCNU), inhibitors or uncouplers of mitochondrial respiration, and drugs that increase reactive oxygen species (ROS), e.g., adriamycin, in standard dosages with standard routes of administration.

GSNOR inhibitors may also be co-administered with a phosphodiesterase inhibitor (e.g., rolipram, cilomilast, roflumilast, Viagra® (sildenifil citrate), Clalis® (tadalafil), Levitra® (vardenifil), etc.), a β-agonist, a steroid, or a leukotriene antagonist (LTD-4). Those skilled in the art can readily determine the appropriate therapeutically effective amount depending on the disorder to be ameliorated.

GSNOR inhibitors may be used as a means to improve β-adrenergic signaling. In particular, inhibitors of GSNOR alone or in combination with β-agonists could be used to treat or protect against heart failure, or other vascular disorders such as hypertension and asthma. GSNOR inhibitors can also be used to modulate G protein coupled receptors (GPCRs) by potentiating Gs G-protein, leading to smooth muscle relaxation (e.g., airway and blood vessels), and by attenuating Gq G-protein, and thereby preventing smooth muscle contraction (e.g., in airway and blood vessels).

The therapeutically effective amount for the treatment of a subject afflicted with a disorder ameliorated by NO donor therapy is the GSNOR inhibiting amount in vivo that causes amelioration of the disorder being treated or protects against a risk associated with the disorder. For example, for asthma, a therapeutically effective amount is a bronchodilating effective amount; for cystic fibrosis, a therapeutically effective amount is an airway obstruction ameliorating effective amount; for ARDS, a therapeutically effective amount is a hypoxemia ameliorating effective amount; for heart disease, a therapeutically effective amount is an angina relieving or angiogenesis inducing effective amount; for hypertension, a therapeutically effective amount is a blood pressure reducing effective amount; for ischemic coronary disorders, a therapeutic amount is a blood flow increasing effective amount; for atherosclerosis, a therapeutically effective amount is an endothelial dysfunction reversing effective amount; for glaucoma, a therapeutic amount is an intraocular pressure reducing effective amount; for diseases characterized by angiogenesis, a therapeutically effective amount is an angiogenesis inhibiting effective amount; for disorders where there is risk of thrombosis occurring, a therapeutically effective amount is a thrombosis preventing effective amount; for disorders where there is risk of restenosis occurring, a therapeutically effective amount is a restenosis inhibiting effective amount; for chronic inflammatory diseases, a therapeutically effective amount is an inflammation reducing effective amount; for disorders where there is risk of apoptosis occurring, a therapeutically effective amount is an apoptosis preventing effective amount; for impotence, a therapeutically effective amount is an erection attaining or sustaining effective amount; for obesity, a therapeutically effective amount is a satiety causing effective amount; for stroke, a therapeutically effective amount is a blood flow increasing or a TIA protecting effective amount; for reperfusion injury, a therapeutically effective amount is a function increasing effective amount; and for preconditioning of heart and brain, a therapeutically effective amount is a cell protective effective amount, e.g., as measured by troponin or CPK.

The therapeutically effective amount for the treatment of a subject afflicted with pathologically proliferating cells means a GSNOR inhibiting amount in vivo which is an antiproliferative effective amount. Such antiproliferative effective amount as used herein means an amount causing reduction in rate of proliferation of at least about 20%, at least about 10%, at least about 5%, or at least about 1%.

I. Uses in an Apparatus

The compounds of the present invention or a pharmaceutically acceptable salt thereof, or a prodrug, or a stereoisomer, or metabolite thereof, can be applied to various apparatus in circumstances when the presence of such compounds would be beneficial. Such apparatus can be any device or container, for example, implantable devices in which a compound of the invention can be used to coat a surgical mesh or cardiovascular stent prior to implantation in a patient. The compounds of the invention can also be applied to various apparatus for in vitro assay purposes or for culturing cells.

The compounds of the present invention or a pharmaceutically acceptable salt thereof, or a prodrug, or a stereoisomer, or metabolite thereof can also be used as an agent for the development, isolation or purification of binding partners to compounds of the invention, such as antibodies, natural ligands, and the like. Those skilled in the art can readily determine related uses for the compounds of the present invention.

EXAMPLES

The following examples are given to illustrate the present invention. It should be understood, however, that the invention is not to be limited to the specific conditions or details described in these examples. Throughout the specification, any and all references to a publicly available document, including a U.S. patent, are specifically incorporated by reference.

Examples 1-14 list representative novel thiophene analogs of Formula I useful as GSNOR inhibitors of the invention. Exemplary schemes below illustrate some general methods of making the thiophene analogs of the invention. Synthetic methods that can be used to prepare each compound are described in Examples 1-14. Supporting mass spectrometry data and/or proton NMR data for each compound is also included in Examples 1-14. Synthetic details for corresponding Intermediates are detailed in Example 15.

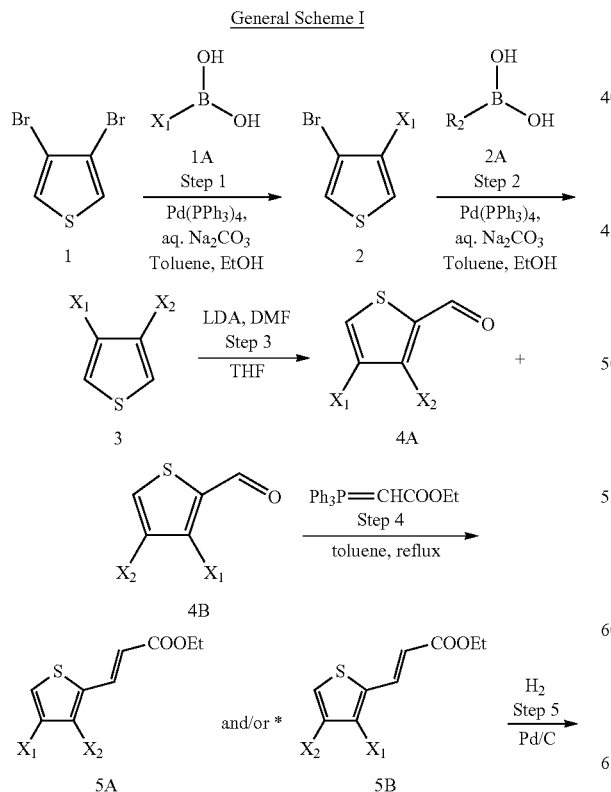

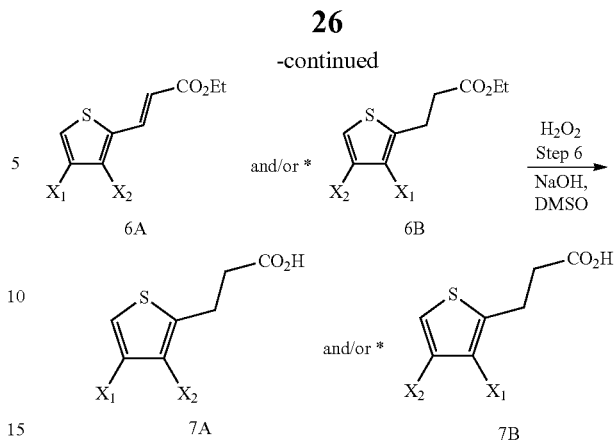

* in some cases the isomer pair gerated in Step 3 was separated after step 3, step 4, or step 5, and only one of them was taken through the rest of the synthesis. In other cases, both were carried through until the end to produce two products.

See Example 1 below for a representative detailed description of Scheme I.

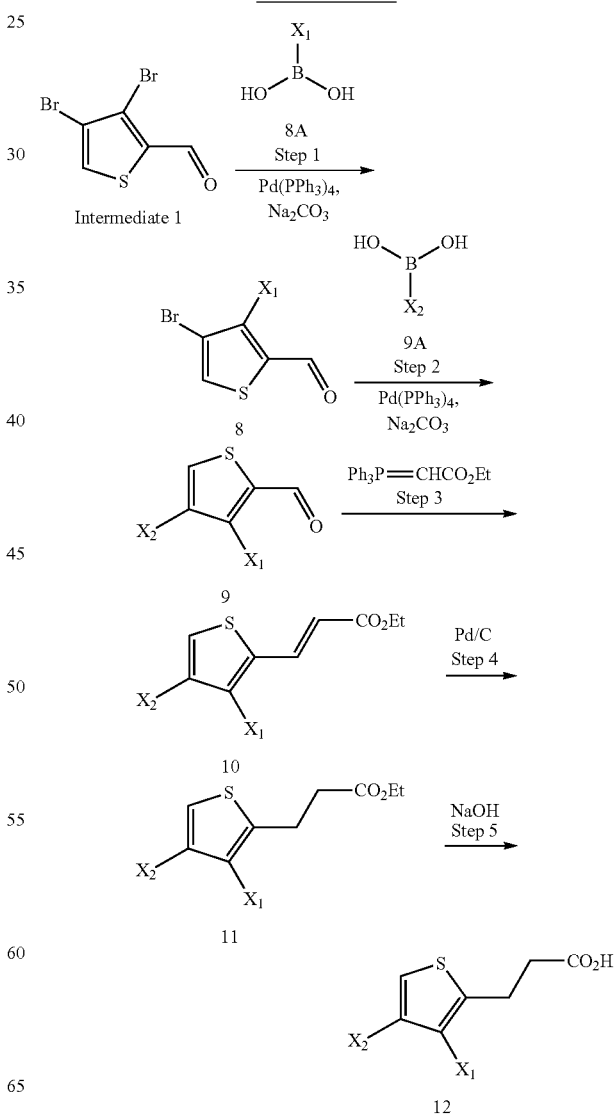

See Example 4 for a representative detailed description of Scheme II.

General Scheme III

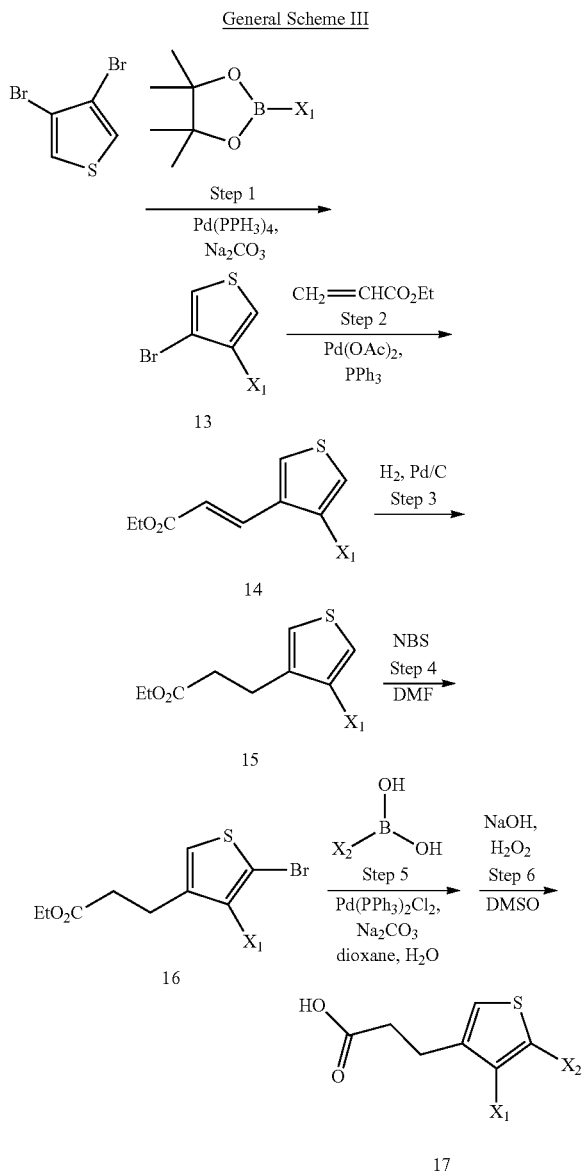

See Example 14 for a representative detailed description of Scheme III.

Example 1

3-(3-(4-carbamoyl-2-methylphenyl)-4-(4-methoxyphenyl)thiophen-2-yl)propanoic acid

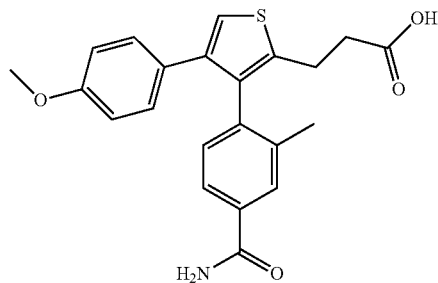 [SMILES: COc1ccc(-c2csc(CCC(=O)O)c2-c2ccc(C(N)=O)cc2C)cc1]

Step 1 of General Scheme I: Synthesis of 3-bromo-4-(4-methoxyphenyl)thiophene (2, $X_1$=4-methoxyphenyl)

To a mixture of 3,4-dibromothiophene (Scheme I, 1) (5 g, 20.7 mmol), 4-methoxyphenylboronic acid (Scheme I, 2, $X_1$=4-methoxyphenyl) (3.14 g, 20.7 mmol), sodium carbonate (4.38 g, 41.3 mmol), toluene (100 mL), in a mixture of ethanol (60 mL) and water (40 mL) was added Pd(PPh$_3$)$_4$ (2.02 g, 1.75 mmol) under nitrogen. The mixture was stirred at 75° C. for 13 h, poured into water (60 mL), and extracted with ethyl acetate (60 mL×3). The organic extracts were dried over anhydrous magnesium sulfate (10 g), evaporated, and purified by column chromatography on silica gel (petroleum ether/ethyl acetate=150:1) to give 3-bromo-4-(4-methoxyphenyl)thiophene (Scheme 1, 2, $X_1$=4-methoxyphenyl) (1.7 g, yield 30.6%). $^1$H NMR (DMSO-d$_6$ 400 MHz): δ 7.84 (d, J=3.2 Hz, 1H), 7.64 (d, J=3.2 Hz, 1H), 7.42 (d, J=8.8 Hz, 2H), 6.97 (d, J=8.8 Hz, 2H), 3.78 (s, 3H).

Step 2 of General Scheme I: Synthesis of 4-(4-(4-methoxyphenyl)thiophen-3-yl)-3-methylbenzonitrile (3, $X_1$=4-methoxyphenyl, $X_2$=4-cyano-2-methylphenyl)

To a mixture of 3-bromo-4-(4-methoxyphenyl)thiophene (Scheme I, 2, $X_1$=4-methoxyphenyl) (1.7 g, 6.316 mmol), 4-cyano-2-methylphenylboronic acid (Scheme I, 2A, $X_2$=4-cyano-2-methylphenyl) (1.535 g, 6.316 mmol), sodium carbonate (1.34 g, 12.63 mmol), toluene (60 mL) in a mixture of ethanol (36 mL) and water (24 mL) under nitrogen was added Pd(PPh$_3$)$_4$ (0.7 g, 0.606 mmol). The mixture was stirred at 80° C. for 5 h, poured into water (50 mL), and extracted with ethyl acetate (50 mL×3). The organic extracts were dried over anhydrous magnesium sulfate (6 g), evaporated, and purified by column chromatography on silica gel (petroleum ether/ethyl acetate=50:1) to give 4-(4-(4-methoxyphenyl)thiophen-3-yl)-3-methylbenzonitrile (Scheme I, 3, $X_1$=4-methoxyphenyl, $X_2$=4-cyano-2-methylphenyl) (1.34 g, yield 69.4%). $^1$H NMR (DMSO-d$_6$ 400 MHz): δ 7.68-7.65 (m, 3H), 7.58 (d, J=3.2 Hz, 1H), 7.33 (d, J=8.0 Hz, 1H), 6.98 (d, J=8.8 Hz, 2H), 6.80 (d, J=8.8 Hz, 2H), 3.70 (s, 3H), 1.79 (s, 3H).

Step 3 of General Scheme I: Synthesis of 4-(2-formyl-4-(4-methoxyphenyl)thiophen-3-yl)-3-methylbenzonitrile (4B, $X_1$=4-methoxyphenyl, $X_2$=4-cyano-2-methylphenyl)

A solution of freshly prepared LDA (0.8 mL, 1.64 mmol) in anhydrous tetrahydrofuran (7 mL) was added slowly a solution of 4-(4-(4-methoxyphenyl)thiophen-3-yl)-3-methylbenzonitrile (Scheme I, 3, $X_1$=4-methoxyphenyl, $X_2$=4-cyano-2-methylphenyl) (500 mg, 1.637 mmol) in anhydrous tetrahydrofuran (6 mL) under nitrogen at −78° C. After being stirred for 15 min., a solution of dimethylformamide (0.14 mL, 1.804 mmol) in anhydrous tetrahydrofuran (3 mL) was dropwise added. The resulting mixture was stirred for 1 h at −78° C., and at room temperature for 3 h. The reaction was quenched with water (50 mL), and extracted with ethyl acetate (40 mL×3). The combined organic extracts were washed with water (30 mL), brine (50 mL), dried over anhydrous sodium sulfate, evaporated, and purified by column chromatography (silica gel, petroleum ether/ethyl acetate=20:1) to afford 4-(2-formyl-4-(4-methoxyphenyl)thiophen-3-yl)-3-methylbenzonitrile (Scheme I, 4A, $X_1$=4-methoxyphenyl, $X_2$=4-cyano-2-methylphenyl) (0.16 g, yield 29.3%) as a white solid (confirmed by NOE). $^1$H NMR (DMSO-d$_6$ 400 MHz): δ 9.46 (s, 1H), 8.31 (d, J=1.2 Hz, 1H), 7.83 (s, 2H), 7.67 (d, J=8.8 Hz, 1H), 7.07 (d, J=8.8 Hz, 2H), 6.89 (d, J=8.8 Hz, 2H), 3.77 (s, 3H), 1.94 (s, 3H).

Step 4 of General Scheme I: Synthesis of (E)-ethyl 3-(3-(4-cyano-2-methylphenyl)-4-(4-methoxyphenyl)thiophen-2-yl)acrylate (5A, X$_1$=4-methoxyphenyl, X$_2$=4-cyano-2-methylphenyl)

The mixture of compound 4-(2-formyl-4-(4-methoxyphenyl)thiophen-3-yl)-3-methylbenzonitrile (Scheme I, 4A, X$_1$=4-methoxyphenyl, X$_2$=4-cyano-2-methylphenyl) (0.16 g, 0.48 mmol) and (carbethoxymethylene)triphenylphosphorane (Ph$_3$P=CHCOOEt) (0.17 g, 0.48 mmol) in toluene (15 mL) was heated to 100° C. for 14 h. After being cooled down to room temperature, the reaction mixture was concentrated and purified by silica gel column chromatography (petroleum ether/ethyl acetate=20:1) to afford (E)-ethyl 3-(3-(4-cyano-2-methylphenyl)-4-(4-methoxyphenyl)thiophen-2-yl)acrylate (Scheme I, 5A, X$_1$=4-methoxyphenyl, X$_2$=4-cyano-2-methylphenyl) (0.27 g, yield 100%) as a white solid.

Step 5 of General Scheme I: Synthesis of ethyl 3-(3-(4-cyano-2-methylphenyl)-4-(4-methoxyphenyl)thiophen-2-yl)propanoate (6A, X$_1$=4-methoxyphenyl, X$_2$=4-cyano-2-methylphenyl)

To a solution of (E)-ethyl 3-(3-(4-cyano-2-methylphenyl)-4-(4-methoxyphenyl)thiophen-2-yl)acrylate (Scheme I, 5A, X$_1$=4-methoxyphenyl, X$_2$=4-cyano-2-methylphenyl) (0.27 g, 0.669 mmol) in ethanol (40 mL) was added 10% Pd/C (0.25 g), and the reaction mixture was stirred at 20° C. under 20 Psi of hydrogen for 30 h. The reaction mixture was filtrated, and concentrated to give ethyl 3-(3-(4-cyano-2-methylphenyl)-4-(4-methoxyphenyl)thiophen-2-yl)propanoate (Scheme I, 6A, X$_1$=4-methoxyphenyl, X$_2$=4-cyano-2-methylphenyl) (0.2 g, yield 73.7%). $^1$H NMR (DMSO-d$_6$ 300 MHz): δ7.71 (m, 2H), 7.45-7.40 (m, 2H), 6.92 (m, 2H), 6.75 (m, 2H), 4.03-3.96 (m, 2H), 3.66 (s, 3H), 2.76-2.71 (m, 3H), 1.80 (s, 2H), 1.22 (s, 1H), 1.14-1.09 (m, 3H).

Step 6 of General Scheme I: Synthesis of 3-(3-(4-carbamoyl-2-methylphenyl)-4-(4-methoxyphenyl)thiophen-2-yl)propanoic acid (7A, X$_1$=4-methoxyphenyl, X$_2$=4-carbamoyl-2-methylphenyl)

To a mixture of ethyl 3-(3-(4-cyano-2-methylphenyl)-4-(4-methoxyphenyl)thiophen-2-yl)propanoate (Scheme I, 6A, X$_1$=4-methoxyphenyl, X$_2$=4-cyano-2-methylphenyl) (180 mg, 0.44 mmol), sodium hydroxide (35.52 mg, 0.88 mmol) in a mixture of DMSO (10 mL) and water (3 mL) was added 30% hydrogen peroxide (0.3 mL). The reaction mixture was stirred at 20° C. for 5 h, hydrogen chloride (1.2 mL, 1 mol/L) was added until pH=5, the resulting mixture was extracted with ethyl acetate (10 mL×4). The combined organic layer was washed with brine (15 mL), dried over anhydrous sodium sulfate, evaporated, and purified by preparative HPLC to give Example 1 (Scheme I, 7A, X$_1$=4-methoxyphenyl, X$_2$=4-carbamoyl-2-methylphenyl) (80 mg, yield 45.6%). $^1$H NMR (DMSO-d$_6$ 400 MHz): δ 12.20 (br s, 1H), 7.93 (s, 1H), 7.71-7.67 (m, 2H), 7.40 (s, 1H), 7.931 (s, 1H), 7.23 (d, J=8.0 Hz, 1H), 6.94 (d, J=8.4 Hz, 2H), 6.71 (d, J=8.4 Hz, 2H), 3.64 (s, 3H), 2.72 (m, 2H), 2.40 (m, 2H), 1.81 (s, 3H); MS (ESI): m/z 396.1 [M+H]$^+$.

Example 2

3-(3-(4-carbamoylphenyl)-4-(4-chloro-2-methoxyphenyl)thiophen-2-yl)propanoic acid

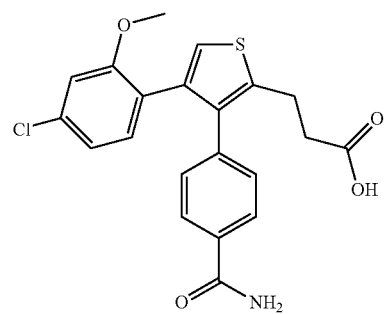 [SMILES: COc1cc(Cl)ccc1-c1csc(CCC(=O)O)c1-c1ccc(C(N)=O)cc1]

Prepared following General Scheme I. The starting material 1A in Step 1 was 4-cyano-phenylboronic acid, and the crude was purified by column chromatography (PE:EtOAc=20:1) to give 4-(4-bromothiophen-3-yl)benzonitrile (8 g, yield 37%). The starting material 2A in Step 2 was 4-chloro-2-methoxyphenylboronic acid, the reaction was heated at 100° C. overnight, and crude was purified by column chromatography (PE:EtOAc=20:1) to give 4-(4-(4-chloro-2-methoxyphenyl)thiophen-3-yl)benzonitrile (0.9 g, yield 73%). Steps 3, 4, 5 and 6 were performed as described in Scheme 1. Both isomers formed in Step 3 were carried through the entire synthesis and were separated after the last step by HPLC. $^1$H NMR (CD$_3$OD 400 MHz): δ 7.78 (d, J=8.4 Hz, 2H), 7.20-7.14 (m, 4H), 6.90 (d, J=8.0 Hz, 1H), 6.78 (s, 1H), 3.11 (t, J=7.6 Hz, 2H), 2.29 (t, J=7.6 Hz, 2H); MS (ESI): m/z 438.0 [M+23]$^+$.

Example 3

3-(3-(4-chloro-2-methoxyphenyl)-4-(4-hydroxyphenyl)thiophen-2-yl)propanoic

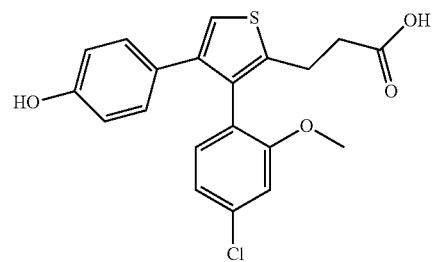 [SMILES: COc1cc(Cl)ccc1-c1c(-c2ccc(O)cc2)csc1CCC(=O)O]

Prepared following General Scheme I. The starting material 1A in Step 1 was 4-hydroxyphenylboronic acid and purification by column chromatography (PE:EtOAc=20:1) gave 4-(4-bromothiophen-3-yl)phenol (2 g, 38% yield). The starting material 2A in Step 2 was 4-chloro-2-methoxyphenylboronic acid and purification by column chromatography (PE:EtOAc=20:1) gave 4-(4-(4-chloro-2-methoxyphenyl)thiophen-3-yl)phenol (0.8 g, yield 65%). After Step 2, the hydroxyl group was protected according to the following description.

Synthesis of 3-(4-chloro-2-methoxyphenyl)-4-(4-(methoxymethoxy)phenyl)thiophene

To a solution of 4-(4-(4-chloro-2-methoxyphenyl)thiophen-3-yl)phenol (700 mg, 2.1 mmol) in anhydrous THF (5 mL) was added NaH (90 mg, 2.3 mmol) at 0° C. After the mixture was stirred at the temperature for 0.5 h, chloro(methoxy)methane (184 mg, 2.3 mmol) was added. The mixture was stirred at 0° C. for 1 hour, and at room temperature for 2 hours. When TLC indicated the starting material was consumed, the mixture was quenched with water, and extracted with EtOAc. The organic layer was dried over $Na_2SO_4$ and concentrated to give the crude product, which was purified by column to give 3-(4-chloro-2-methoxyphenyl)-4-(4-(methoxymethoxy)phenyl)thiophene (720 mg, 90%) which was taken forward to Step 3.

Followed Step 3 described in Scheme I, to give 3-(4-chloro-2-methoxyphenyl)-4-(4-(methoxymethoxy)phenyl)thiophene-2-carbaldehyde (290 mg, yield 37%). Followed Step 4 described in Scheme 1, where crude was purified by column chromatography (PE: EtOAc=15:1) to give (E)-ethyl 3-(3-(4-chloro-2-methoxyphenyl)-4-(4-(methoxymethoxy)phenyl)thiophen-2-yl)acrylate (280 mg, yield 82%). Step 5 of Scheme 1 gave ethyl 3-(3-(4-chloro-2-methoxyphenyl)-4-(4-(methoxymethoxy)phenyl)thiophen-2-yl)propanoate (220 mg, yield 78%). Step 6 of Scheme 1 gave crude 3-(3-(4-chloro-2-methoxyphenyl)-4-(4-(methoxymethoxy)phenyl)thiophen-2-yl)propanoic acid (190 mg, yield 92%). The final step was a deprotection of the alcohol and is described here.

Synthesis of 3-(3-(4-chloro-2-methoxyphenyl)-4-(4-hydroxyphenyl)thiophen-2-yl)propanoic acid To a solution of 3-(3-(4-chloro-2-methoxyphenyl)-4-(4-(methoxymethoxy)phenyl)thiophen-2-yl)propanoic acid (190 mg, 0.44 mmol) in THF (5 mL) was added HCl (1 mL, 12 M) and the mixture was stirred at room temperature for 2 hours. The mixture was diluted with water, extracted with EtOAc, and concentrated to give the crude compound, which was purified by preparative HPLC (Column: YMC ODS-AQ 150×30 cm, 5 μm; Retention Time: 15 min; Mobile phase: from 38% MeCN in water (0.05% TFA) to 68% MeCN in water (0.05% TFA); Wavelength: 220 nm, 254 nm; sample dissolved in DMSO) to give 3-(3-(4-chloro-2-methoxyphenyl)-4-(4-hydroxyphenyl)thiophen-2-yl)propanoic acid (47.5 mg, yield 28%). $^1$H NMR ($CD_3OD$ 400 MHz): δ 7.11 (s, 1H), 6.99 (d, J=1.6 Hz, 1H), 6.97-6.92 (m, 2H), 6.89 (d, J=8.4 Hz, 2H), 6.58 (d, J=8.8 Hz, 2H), 3.58 (s, 3H), 2.90 (t, J=8.0 Hz, 2H), 2.50 (t, J=8.0 Hz, 2H); MS (ESI): m/z $[M+1]^+$= 389.1.

Example 4

3-(4-(4-chloro-2-methoxyphenyl)-3-(4-hydroxyphenyl)thiophen-2-yl)propanoic

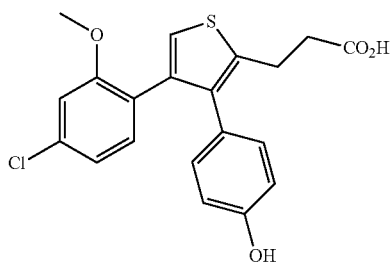 [SMILES: COc1cc(Cl)ccc1-c1csc(CCC(=O)O)c1-c1ccc(O)cc1]

Step 1 of General Scheme II: Synthesis of 4-bromo-3-(4-hydroxyphenyl)thiophene-2-carbaldehyde A mixture of 3,4-dibromothiophene-2-carbaldehyde (see Intermediate 1 (see Example 15 for Intermediate synthesis)) (2.0 g, 7.5 mmol), 4-hydroxyphenylboronic acid (Scheme II, 8A, $X_1$=4-hydroxyphenyl) (1.0 g, 7.5 mmol), $Na_2CO_3$ (1.6 g, 15 mmol), and $Pd(PPh_3)_4$ (431 mg, 0.37 mmol) in toluene/EtOH/$H_2O$ (30 mL, 5:3:2) was heated to 80° C. and stirred overnight under nitrogen. When TLC indicated that the starting material was consumed, the mixture was diluted with water, neutralized to pH=4-5 with HCl (1M), extracted with EtOAc, concentrated, and purified by column chromatography (PE:EtOAc=20:1) to give 4-bromo-3-(4-hydroxyphenyl)thiophene-2-carbaldehyde (Scheme II, 8, $X_1$=4-hydroxyphenyl) (350 mg, yield 17%) as a white solid. $^1$H NMR (DMSO-$d_6$ 400 MHz): δ9.90 (s, 1H), 9.53 (s, 1H), 8.33 (s, 1H), 7.33 (d, J=8.4 Hz, 2H), 6.91 (d, J=8.4 Hz, 2H).

Step 2 of General Scheme II: Synthesis of 4-bromo-3-(4-hydroxyphenyl)thiophene-2-carbaldehyde A mixture of 4-bromo-3-(4-hydroxyphenyl)thiophene-2-carbaldehyde (Scheme II, 8, $X_1$=4-hydroxyphenyl) (300 mg, 1.1 mmol), 4-chloro-2-methoxyphenylboronic acid (Scheme II, 9A, $X_2$=4-chloro-2-methoxyphenyl) (237 mg, 1.3 mmol), $Na_2CO_3$ (225 mg, 2.2 mmol), and $Pd(PPh_3)_4$ (61 mg, 0.05 mmol) in toluene/EtOH/$H_2O$ (10 mL, 5:3:2) was heated at 100° C., and stirred overnight under nitrogen. When TLC indicated that the starting material was consumed, the mixture was diluted with water, neutralized to pH=4-5 with HCl (1M), extracted with EtOAc, concentrated, and purified by column chromatography (PE:EtOAc=20:1) to give 4-bromo-3-(4-hydroxyphenyl)thiophene-2-carbaldehyde (Scheme II, 9, $X_1$=4-hydroxyphenyl, $X_2$=4-chloro-2-methoxyphenyl) (290 mg, yield 79%) as a white solid. $^1$H NMR (DMSO-$d_6$ 400 MHz): δ 9.54 (s, 1H), 9.50 (s, 1H), 7.90 (s, 1H), 6.98 (d, J=8.0 Hz, 1H), 6.89 (m, 4H), 6.58 (d, J=8.4 Hz, 2H), 3.29 (s, 3H).

Step 3 of General Scheme II: Synthesis of (E)-ethyl 3-(4-(4-chloro-2-methoxyphenyl)-3-(4-hydroxyphenyl)thiophen-2-yl)acrylate A mixture of 4-bromo-3-(4-hydroxyphenyl)thiophene-2-carbaldehyde (290 mg, 0.84 mmol) and (carbethoxymethylene)triphenylphosphorane (322 mg, 0.93 mmol) in toluene (10 mL) was stirred at 100° C. overnight. When TLC indicated the starting material was consumed, the mixture was concentrated and purified by column chromatography (PE:EtOAc=15:1) to give (E)-ethyl 3-(4-(4-chloro-2-methoxyphenyl)-3-(4-hydroxyphenyl)thiophen-2-yl)acrylate (Scheme II, 10, $X_1$=4-hydroxyphenyl, $X_2$=4-chloro-2-methoxyphenyl) (280 mg, yield 80%). $^1$H NMR (DMSO-$d_6$ 400 MHz TMS): δ9.56 (s, 1H), 7.65 (s, 1H), 7.51 (d, J=15.6 Hz, 1H), 7.08 (d, J=8.0 Hz, 1H), 6.95 (d, J=8.0 Hz, 2H), 6.81 (d, J=8.4 Hz, 2H), 6.71 (d, J=8.4 Hz, 2H), 6.26 (d, J=15.6 Hz, 1H), 4.13 (q, J=7.2 Hz, 2H), 3.41 (s, 3H), 1.20 (t, J=7.2 Hz, 3H).

Step 4 of General Scheme II: Synthesis of ethyl 3-(4-(4-chloro-2-methoxyphenyl)-3-(4-hydroxyphenyl)thiophen-2-yl)propanoate To a solution of (E)-ethyl 3-(4-(4-chloro-2-methoxyphenyl)-3-(4-hydroxyphenyl)thiophen-2-yl)acrylate (280 mg, 0.61 mmol) in EtOH (5 mL) was added Pd/C (50 mg). After the mixture was stirred at room temperature under $H_2$ atmosphere for 4 hours, the mixture was filtered and concentrated in vacuo to give ethyl 3-(4-(4-chloro-2-methoxyphenyl)-3-

(4-hydroxyphenyl)thiophen-2-yl)propanoate (Scheme II, 11, $X_1$=4-hydroxyphenyl, $X_2$=4-chloro-2-methoxyphenyl) (220 mg, yield 78%). $^1$H NMR (DMSO-$d_6$ 400 MHz): δ 9.34 (s, 1H), 7.26 (s, 1H), 7.01 (d, J=8.4 Hz, 1H), 6.90 (d, J=8.8 Hz, 2H), 6.79 (d, J=8.0 Hz, 2H), 6.64 (d, J=8.4 Hz, 2H), 4.04 (q, J=7.2 Hz, 2H), 3.40 (s, 3H), 2.96 (t, J=7.6 Hz, 2H), 2.55 (t, J=7.6 Hz, 2H), 1.16 (t, J=7.2 Hz, 3H).

Step 5 of General Scheme II: Synthesis of 3-(4-(4-chloro-2-methoxyphenyl)-3-(4-hydroxyphenyl)thiophen-2-yl)propanoic acid To a solution of ethyl 3-(4-(4-chloro-2-methoxyphenyl)-3-(4-hydroxyphenyl)thiophen-2-yl)propanoate (220 mg, 0.53 mmol) in EtOH (5 mL) was added NaOH (42 mg, 1.06 mmol), and the mixture was stirred at room temperature for 2 hours. The mixture was diluted with water, neutralized to pH=4-5, extracted with EtOAc, and concentrated to give 3-(4-(4-chloro-2-methoxyphenyl)-3-(4-hydroxyphenyl)thiophen-2-yl)propanoic acid (Scheme II, 12, $X_1$=4-hydroxyphenyl, $X_2$=4-chloro-2-methoxyphenyl) (127.42 mg, yield 62%). $^1$H NMR (DMSO-$d_6$ 400 MHz): δ 9.36 (br, 1H), 7.25 (s, 1H), 7.01 (d, J=8.0 Hz, 1H), 6.91-6.88 (m, 2H), 6.79 (d, J=8.4 Hz, 2H), 6.64 (d, J=8.4 Hz, 2H), 3.40 (s, 3H), 2.92 (t, J=7.2 Hz, 2H), 2.47 (t, J=7.2 Hz, 2H); MS (ESI): m/z [M+1]$^+$=389.0.

Example 5

3-(4-(4-chloro-2-methoxyphenyl)-3-(4-(methylsulfonamido)phenyl)thiophen-2-yl)propanoic acid

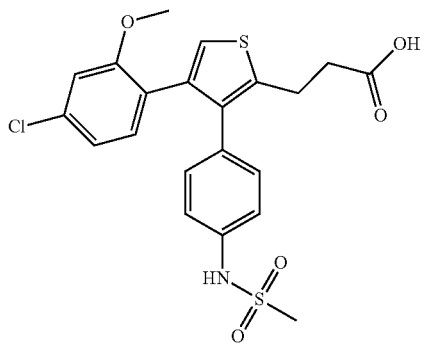 [SMILES: COc1cc(Cl)ccc1-c1csc(CCC(=O)O)c1-c1ccc(NS(C)(=O)=O)cc1]

Prepared following General Scheme II. The starting material 8A in Step 1 was 4-amino-2-methylphenylboronic acid, and the crude was purified by column chromatography (PE: EtOAc=5:1) to give 3-(4-aminophenyl)-4-bromothiophene-2-carbaldehyde (1.5 g, yield 47.8%). The starting material 9A in Step 2 was 4-chloro-2-methoxyphenylboronic acid, and crude was purified by column chromatography (PE: EtOAc=3:1) to give 3-(4-aminophenyl)-4-(4-chloro-2-methoxyphenyl)thiophene-2-carbaldehyde (300 mg, yield, 49.3%). Step 3 of Scheme II was followed, with crude purified by column chromatography (PE:EtOAc=3:1) to give (E)-ethyl 3-(3-(4-aminophenyl)-4-(4-chloro-2-methoxyphenyl)thiophen-2-yl)acrylate (300 mg, yield 83%). The amine of this product was then mesylated following the procedure described here.

Synthesis of (E)-ethyl 3-(4-(4-chloro-2-methoxyphenyl)-3-(4-(methylsulfonamido)phenyl)thiophen-2-yl)acrylate To a mixture of (E)-ethyl 3-(3-(4-aminophenyl)-4-(4-chloro-2-methoxyphenyl)thiophen-2-yl)acrylate (300 mg, 0.73 mmol) and TEA (75 mg, 0.73 mmol) in DCM (10 mL) was added MsCl (108 mg, 0.95 mmol), and the mixture was stirred at room temperature overnight. The reaction solution was washed with brine, dried over sodium sulfate, and concentrated under reduced pressure to give (E)-ethyl 3-(4-(4-chloro-2-methoxyphenyl)-3-(4-(methylsulfonamido) phenyl)thiophen-2-yl)acrylate, which was used in the next step without further purification.

Following Step 4 of General Scheme II gave ethyl 3-(4-(4-chloro-2-methoxyphenyl)-3-(4-(methylsulfonamido)phenyl)thiophen-2-yl)propanoate (200 mg, yield 80.0%). Following Step 5 of Scheme II, where the mixture was acidified to pH=7, and purified by preparative HPLC gave 29 mg of Example 5 (yield 15.3%). $^1$H NMR (CD$_3$OD, 400 MHz): δ 7.15-7.17 (m, 3H), 7.10 (d, J=8.0 Hz, 1H), 7.03 (d, J=8.4 Hz, 2H), 6.88 (d, J=8.4 Hz, 1H), 6.80 (s, 1H), 3.40 (s, 3H), 3.09 (t, J=7.6 Hz, 2H), 2.58 (t, J=7.6 Hz, 2H); MS (ESI): m/z 488.1 [M+1]$^+$.

Example 6

3-(4-(4-carbamoylphenyl)-3-(4-(2-methyl-1H-imidazol-1-yl)phenyl)thiophen-2-yl)propanoic acid

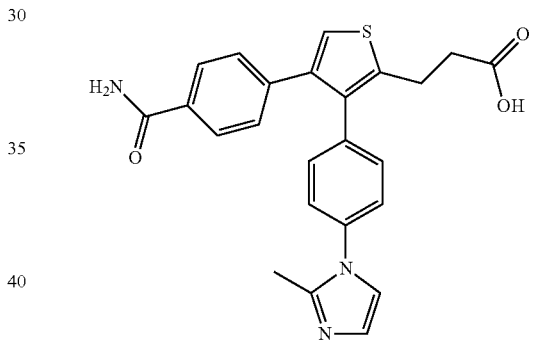

Followed the procedure described in General Scheme II, with modification. Step 1 was followed where the starting material was 4-(4-bromo-5-formylthiophen-3-yl)benzonitrile (Intermediate 3) instead of 3,4-dibromothiophene-2-carbaldehyde (Intermediate I) and starting material 8A was Intermediate 2 (2-methyl-1-(4-(4,4,5,5-tetramethyl-1,3,2-dioxaborolan-2-yl)phenyl)-1H-imidazole). After purification by column chromatography (DCM:MeOH=30:1) the desired 4-(5-formyl-4-(4-(2-methyl-1H-imidazol-1-yl)phenyl) thiophen-3-yl)benzonitrile (500 mg, yield 60%) was obtained. Step 3 of Scheme II was then followed with column conditions (PE: EtOAc=1:2) to afford (E)-ethyl 3-(4-(4-cyanophenyl)-3-(4-(2-methyl-1H-imidazol-1-yl)phenyl) thiophen-2-yl)acrylate (600 mg, yield 100%). Step 4 of Scheme II gave 450 mg of product (yield 75%) followed by Step 5 (with purification by prep-HPLC) gave Example 6 (45.98 mg, 10% yield). $^1$H NMR (CD$_3$OD 400 MHz): δ 7.65-7.63 (m, 3H), 7.53 (s, 1H), 7.47 (d, J=8.0 Hz, 2H), 7.38-7.34 (m, 3H), 7.13 (d, J=8.0 Hz, 2H), 3.04 (t, J=7.6 Hz, 2H), 2.56-2.52 (m, 5H); MS (ESI): m/z 432.0 [M+1]$^+$.

Example 7

3-(3-(4-carbamoyl-2-methylphenyl)-4-(4-(2-methyl-1H-imidazol-1-yl)phenyl)thiophen-2-yl)propanoic acid

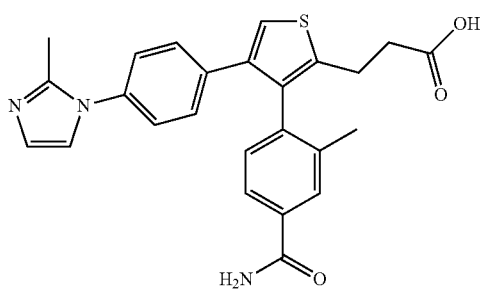 [SMILES: Cc1cc(C(N)=O)ccc1-c1c(-c2ccc(-n3ccnc3C)cc2)csc1CCC(=O)O]

Prepared following General Scheme II. The starting material 8A in Step 1 was 4-cyano-2-methylphenylboronic acid, and column conditions for Step 1 was (PE: EtOAc=10:1) to give 4-(4-bromo-2-formylthiophen-3-yl)-3-methylbenzonitrile (2 g, yield 88%). The starting material 9A in Step 2 was Intermediate 2 (2-methyl-1-(4-(4,4,5,5-tetramethyl-1,3,2-dioxaborolan-2-yl)phenyl)-1H-imidazole), and crude was purified by column chromatography (PE:EtOAc=1:2) to give 4-(2-formyl-4-(4-(2-methyl-1H-imidazol-1-yl)phenyl)thiophen-3-yl)-3-methylbenzonitrile (0.55 g, yield 60%). Step 3 of scheme II was followed, with purification by column chromatography (PE:EtOAc=1:1) to afford (E)-ethyl 3-(3-(4-cyano-2-methylphenyl)-4-(4-(2-methyl-1H-imidazol-1-yl)phenyl)thiophen-2-yl)acrylate (600 mg, yield 92%). Following Step 4 of General Scheme II gave 400 mg of desired (66% yield). Following Step 5 of Scheme II, where crude was purified by preparative HPLC, gave 26.4 mg of Example 7 (yield 9%). $^1$H NMR (DMSO-d$_6$ 400 MHz): δ 7.99 (s, 1H), 7.87 (s, 1H), 7.79-7.73 (m, 4H), 7.47 (d, J=8.4 Hz, 2H), 7.39 (s, 1H), 7.32-7.30 (m, 3H), 2.84-2.69 (m, 2H), 2.50-2.42 (m, 5H), 1.89 (s, 3H); MS (ESI): m/z 446.1 [M+1]$^+$.

Example 8

3-(3-(4-carbamoylphenyl)-4-(4-(2-methyl-1H-imidazol-1-yl)phenyl)thiophen-2

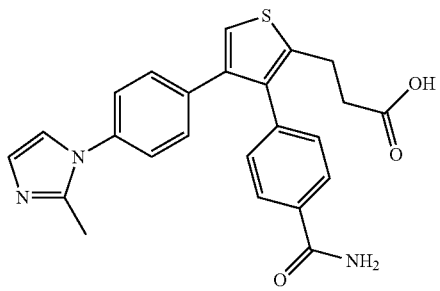 [SMILES: Cc1nccn1-c1ccc(-c2csc(CCC(=O)O)c2-c2ccc(C(N)=O)cc2)cc1]

Prepared following General Scheme II. The starting material 8A in Step 1 was 4-cyanophenylboronic acid. The starting material 9A in Step 2 was Intermediate 2 (2-methyl-1-(4-(4,4,5,5-tetramethyl-1,3,2-dioxaborolan-2-yl)phenyl)-1H-imidazole), and crude was purified by column chromatography (PE:EtOAc=2:1) to give 4-(2-formyl-4-(4-(2-methyl-1H-imidazol-1-yl)phenyl)thiophen-3-yl)benzonitrile (300 mg, yield 47%). Step 3 of scheme II was followed, with purification by column chromatography (PE:EtOAc=1:2) to afford (E)-ethyl 3-(3-(4-cyanophenyl)-4-(4-(2-methyl-1H-imidazol-1-yl)phenyl)thiophen-2-yl)acrylate (250 mg, yield 70%). Following Step 4 of General Scheme II gave ethyl 3-(3-(4-cyanophenyl)-4-(4-(2-methyl-1H-imidazol-1-yl)phenyl)thiophen-2-yl)propanoate (200 mg, yield 80%) and Step 5 of Scheme II, where crude was purified by preparative HPLC gave 166 mg of Example 8 (yield 85%). $^1$H NMR (CD$_3$OD 300 MHz): δ 7.88 (d, J=8.4 Hz, 2H), 7.64 (d, J=2.1 Hz, 1H), 7.58 (d, J=2.1 Hz, 1H), 7.50 (s, 1H), 7.43-7.35 (m, 4H), 7.29 (d, J=8.4 Hz, 2H), 3.09 (t, J=7.2 Hz, 2H), 2.61-2.55 (m, 5H); MS (ESI): m/z 432.0 [M+1]$^+$.

Example 9

3-(4-(4-(2-methyl-1H-imidazol-1-yl)phenyl)-3-(2-methyl-4-(methylsulfonamido)phenyl)thiophen-2-yl)propanoic acid

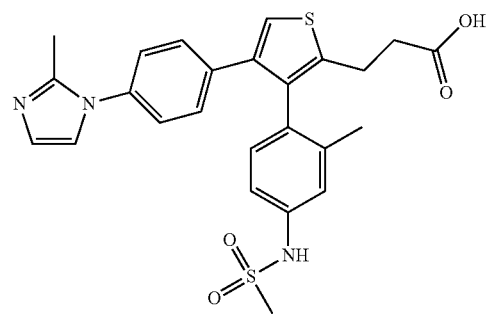 [SMILES: Cc1cc(NS(C)(=O)=O)ccc1-c1c(-c2ccc(-n3ccnc3C)cc2)csc1CCC(=O)O]

Followed the procedure described in General Scheme II, with modification. Step 1 was followed where the starting material was N-(4-(4-bromo-2-formylthiophen-3-yl)-3-methylphenyl)methanesulfonamide (Intermediate 4) instead of 3,4-dibromothiophene-2-carbaldehyde (Intermediate I) and starting material 8A was Intermediate 2 (2-methyl-1-(4-(4,4,5,5-tetramethyl-1,3,2-dioxaborolan-2-yl)phenyl)-1H-imidazole). After purification by column chromatography (PE:EtOAc=1:2) N-(4-(2-formyl-4-(4-(2-methyl-1H-imidazol-1-yl)phenyl)thiophen-3-yl)-3-methylphenyl)methanesulfonamide (200 mg, yield 30%) was obtained. Step 3 of Scheme II was then followed with column conditions (PE: EtOAc=1:2) to afford (E)-ethyl 3-(4-(4-(2-methyl-1H-imidazol-1-yl)phenyl)-3-(4-(methylsulfonamido)phenyl)thiophen-2-yl)acrylate (190 mg, yield 82%). Step 4 of Scheme II gave 140 mg of product (yield 77%) followed by Step 5 (with purification by prep-HPLC) gave Example 9 (41.9 mg, 31% yield). $^1$H NMR (DMSO-d$_6$ 400 MHz): δ 9.76 (s, 1H), 7.82 (d, J=2.0 Hz, 1H), 7.69 (d, J=2.0 Hz, 1H), 7.66 (s, 1H), 7.43 (d, J=8.8 Hz, 2H), 7.27 (d, J=8.8 Hz, 2H), 7.14 (d, J=8.4 Hz, 1H), 7.07 (dd, J=2.0 Hz, J=8.0 Hz, 1H), 7.01 (d, J=2.0 Hz, 1H), 2.97 (s, 3H), 2.79-2.68 (m, 2H), 2.44-2.38 (m, 5H), 1.78 (s, 3H); MS (ESI): m/z 496.0 [M+1]$^+$.

Example 10

3-(4-(4-chloro-2-methoxyphenyl)-3-(2-methyl-4-(methylsulfonamido)phenyl)thiophen-2-yl)propanoic acid

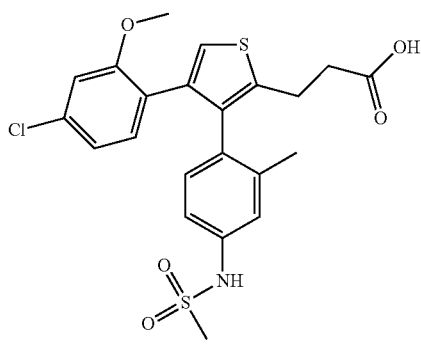 [SMILES: COc1cc(Cl)ccc1-c1csc(CCC(=O)O)c1-c1ccc(NS(C)(=O)=O)cc1C]

Followed the procedure described in General Scheme II, with modification. Step 1 was followed where the starting material was N-(4-(4-bromo-2-formylthiophen-3-yl)-3-methylphenyl)methanesulfonamide (Intermediate 4) instead of 3,4-dibromothiophene-2-carbaldehyde (Intermediate I), starting material 8A was 4-chloro-2-methoxyphenylboronic acid. After purification by column chromatography (PE:EtOAc=3:1) N-(4-(4-(4-chloro-2-methoxyphenyl)-2-formylthiophen-3-yl)-3-methylphenyl)methanesulfonamide (380 mg, yield 365.2%) was obtained. Step 3 of Scheme II was then followed with column conditions (PE: EtOAc=3:1) to afford (E)-ethyl 3-(4-(4-chloro-2-methoxyphenyl)-3-(2-methyl-4-(methylsulfonamido)phenyl)thiophen-2-yl)acrylate (280 mg, yield 63.4%). Step 4 of Scheme II gave 200 mg of product (yield 71%) followed by Step 5 (with purification by prep-HPLC) gave Example 10 (41.9 mg, 13% yield). $^1$H NMR (DMSO-$d_6$ 400 MHz): δ 9.73 (s, 1H), 7.38 (s, 1H), 6.93 (m, 4H), 6.90 (s, 1H), 6.86 (m, 1H), 3.5 (d, 3H), 2.95 (s, 1H), 2.75 (m, 2H), 7.01 (t, J=7.2 Hz, 2H), 1.82 (s, 3H); MS (ESI): m/z 502.0 [M+23]$^+$.

Example 11

3-(4'-(4-carbamoyl-2-methylphenyl)-5-(2-methyl-1H-imidazol-1-yl)-2,3'-bithiophen-5'-yl)propanoic acid

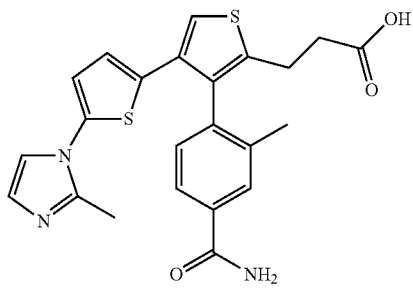 [SMILES: Cc1cc(C(N)=O)ccc1-c1c(-c2ccc(-n3ccnc3C)s2)csc1CCC(=O)O]

Followed the procedure described in General Scheme II, with modification. Followed Scheme II, Step 1 where the starting material 8A was 4-cyano-2-methylphenylboronic acid to give 4-(4-bromo-2-formylthiophen-3-yl)-3-methylbenzonitrile. This was followed by a modification of the second step (tin coupling instead of boronic acid coupling) which is detailed below.

Step 2: A mixture of Intermediate 5 (2-methyl-1-(5-(tributylstannyl)thiophen-2-yl)-1H-imidazole, 580 mg, 1.28 mmol), 4-(4-bromo-2-formylthiophen-3-yl)-3-methylbenzonitrile (392 mg, 1.28 mmol) and tetrakis(triphenylphosphine)palladium (200 mg, 0.17 mmol) in toluene was heated to reflux overnight. The mixture was poured into water and extracted with ethyl acetate. The combined organic layer was concentrated, the residue was purified on silica gel column to give 4-(5'-formyl-5-(2-methyl-1H-imidazol-1-yl)-2,3'-bithiophen-4'-yl)-3-methylbenzonitrile (280 mg, yield 56.2%).

Next followed Step 3 of Scheme II to give (E)-ethyl 3-(4'-(4-cyano-2-methylphenyl)-5-(2-methyl-1H-imidazol-1-yl)-2,3'-bithiophen-5'-yl)acrylate (120 mg, yield 36.4%). Following Step 4 of Scheme II gave ethyl 3-(4'-(4-cyano-2-methylphenyl)-5-(2-methyl-1H-imidazol-1-yl)-2,3'-bithiophen-5'-yl)propanoate. And finally Step 5 of Scheme II was followed (purified directly by preparative HPLC (26-53% acetonitrile+0.1% trifluoroacetic acid in water+0.1% trifluoroacetic acid, over 15 min.)) to give Example 11 (55 mg, 50% yield). $^1$H NMR (CD$_3$OD 400 MHz): δ 7.82 (m, 2H), 7.72 (s, 1H), 7.60 (s, 1H), 7.54 (s, 1H), 7.34 (d, J=7.6 Hz, 1H), 7.16 (d, J=4.0 Hz, 1H), 7.85 (d, J=4.0 Hz, 1H), 2.87 (m, 2H), 2.54 (m, 5H), 2.08 (s, 3H); MS (ESI): m/z 452.0 [M+1]$^+$.

Example 12

3-(5-(2-methyl-1H-imidazol-1-yl)-4'-(2-methyl-4-(methylsulfonamido)phenyl)-2,3'-bithiophen-5'-yl)propanoic acid

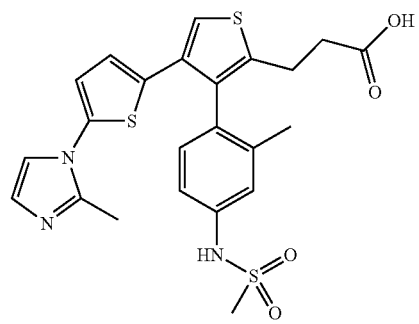 [SMILES: Cc1cc(NS(C)(=O)=O)ccc1-c1c(-c2ccc(-n3ccnc3C)s2)csc1CCC(=O)O]

Prepared following General Scheme II, with modification. Intermediate 4 (N-(4-(4-bromo-2-formylthiophen-3-yl)-3-methylphenyl)methanesulfonamide) was coupled with Intermediate 5 (2-methyl-1-(5-(tributylstannyl)thiophen-2-yl)-1H-imidazole) following the procedure detailed in Example 11, Step 2 to give N-(4-(5'-formyl-5-(2-methyl-1H-imidazol-1-yl)-2,3'-bithiophen-4'-yl)-3-methylphenyl)methanesulfonamide (200 mg, yield 54.5%). Next followed Step 3 of Scheme II to give (E)-ethyl 3-(5-(2-methyl-1H-imidazol-1-yl)-4'-(2-methyl-4-(methylsulfonamido)phenyl)-2,3'-bithiophen-5'-yl)acrylate (180 mg, yield 78.0%). Following Step 4 of Scheme II gave ethyl 3-(5-(2-methyl-1H-imidazol-1-yl)-4'-(2-methyl-4-(methylsulfonamido)phenyl)-2,3'-bithiophen-5'-yl)propanoate (160 mg, yield 88.8%). And finally Step 5 of Scheme II was followed (purified directly by preparative HPLC (26-53% acetonitrile+0.1% trifluoroacetic acid in water+0.1% trifluoroacetic acid, over 15 min.)) to give Example 12 (15 mg, 10% yield). ¹H NMR (DMSO-d₆ 300 MHz): δ 9.85 (s, 1H), 7.80 (s, 1H), 7.38 (s, 1H), 7.10 (m, 5H), 6.83 (d, J=3.9 Hz, 1H), 3.02 (s, 3H), 2.74 (m, 2H), 2.44 (m, 2H), 2.27 (s, 3H), 1.91 (s, 3H); MS (ESI) m/z: 502.2 [M+1]⁺.

Example 13

3-(4-(4-bromophenyl)-3-(4-carbamoyl-2-methylphenyl)thiophen-2-yl)propanoic acid

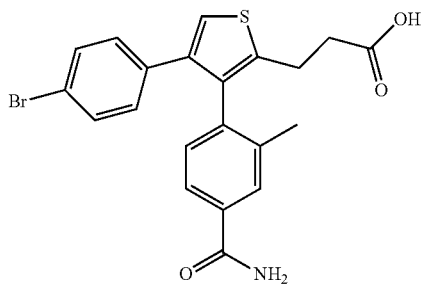 [SMILES: Cc1cc(C(N)=O)ccc1-c1c(-c2ccc(Br)cc2)csc1CCC(=O)O]

Followed the procedure described in General Scheme II, with modification. The starting material 8A in Scheme II, Step 1 was 4-cyano-2-methylphenylboronic acid to give 4-(4-bromo-2-formylthiophen-3-yl)-3-methylbenzonitrile (2.4 g, yield 88.9%). The starting material 9A in Step 2 was 4-aminophenylboronic acid, and the crude was purified by column chromatography (PE: EtOAc=5:1) to give 4-(4-(4-aminophenyl)-2-formylthiophen-3-yl)-3-methylbenzonitrile (1.0 g, yield 64.0%). Step 3 of Scheme II was followed to give crude (E)-ethyl 3-(4-(4-aminophenyl)-3-(4-cyano-2-methylphenyl)thiophen-2-yl)acrylate which was used directly in the next step. Following Step 4 of Scheme II where the crude was purified by column chromatography (PE: EtOAc=5:1) gave ethyl 3-(4-(4-aminophenyl)-3-(4-cyano-2-methylphenyl)thiophen-2-yl)propanoate (330 mg, yield 30.0%). The following modification of Scheme II was made, converting the amino group to bromo:

Synthesis of ethyl 3-(4-(4-bromophenyl)-3-(4-cyano-2-methylphenyl)thiophen-2-yl)propanoate To a mixture of ethyl 3-(4-(4-aminophenyl)-3-(4-cyano-2-methylphenyl)thiophen-2-yl)propanoate (180 mg, 0.46 mmol) in a mixture solvent of HBr (48%, 3 mL) and water (1 mL) was added dropwise a solution of NaNO₂ (32 mg, 0.46 mmol) in water (0.5 mL). Then the mixture was stirred at 0° C. for 1 hour. Then CuBr (66 mg, 0.46 mmol) was added and the mixture was stirred at 0° C. for additional 1 hour. The reaction mixture was extracted with EtOAc and the combined organic layer was dried over Na₂SO₄, concentrated in vacuo to give crude ethyl 3-(4-(4-bromophenyl)-3-(4-cyano-2-methylphenyl)thiophen-2-yl)propanoate, which was used in the next step directly.

Lastly, Step 5 of Scheme II was followed: A mixture of crude ethyl 34444-bromophenyl)-3-(4-cyano-2-methylphenyl)thiophen-2-yl)propanoate (210 mg, 0.46 mmol) in DMSO (3 mL) was added aqueous solution of NaOH (2 M, 1 mL), followed by the addition of H₂O₂ (0.2 mL). The mixture was stirred at room temperature for 10 minutes. The mixture was quenched with saturated aqueous Na₂SO₃ and extracted with a mixture of DCM/iPrOH (3/1). The combined organic layer was dried over Na₂SO₄, concentrated in vacuo. The residue was purified by HPLC (48-78% acetonitrile+0.15% trifluoroacetic acid in water, over 15 min) to afford 3-(4-(4-bromophenyl)-3-(4-carbamoyl-2-methylphenyl)thiophen-2-yl)propanoic acid (17.0 mg, yield 8.3%). ¹H NMR (CD₃OD 400 MHz): δ 7.66 (d, J=8.0 Hz, 1H), 7.62 (s, 1H), 7.26 (d, J=8.0 Hz, 1H), 7.20-7.19 (m, 3H), 7.11-7.08 (m, 2H), 2.62-2.81 (m, 2H), 2.50 (t, J=7.6 Hz, 2H), 1.98 (s, 3H). MS (ESI): m/z 446.0 [M+3]⁺.

Example 14

3-(4-(4-carbamoyl-2-methylphenyl)-5-(4-methoxyphenyl)thiophen-3-yl)propanoic acid

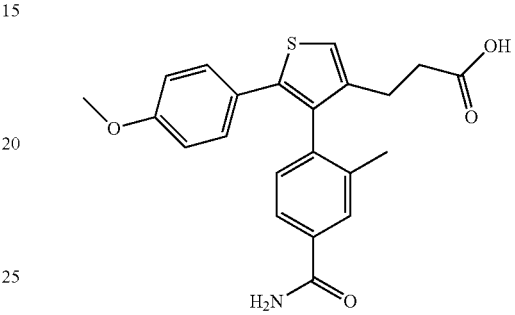

Step 1 of General Scheme III: Synthesis of 4-(4-bromothiophen-3-yl)-3-methylbenzonitrile A mixture of 3,4-dibromothiophene (3 g, 12.5 mmol), 3-methyl-4-(4,4,5,5-tetramethyl-1,3,2-dioxaborolan-2-yl)benzonitrile (2 g, 12.5 mmol), Na₂CO₃ (2.7 g, 25 mmol), Pd(PPh₃)₄ (1.4 g, 1.25 mmol) in a mixture of toluene/EtOH/H₂O (40 mL, 5:3:2) was stirred at 80° C. under nitrogen overnight. The reaction mixture was diluted with EtOAc (80 mL), and washed with water and brine. The organic phase was dried over Na₂SO₄, concentrated in vacuo, and purified on silica gel column (PE: EtOAc=30:1) to afford 4-(4-bromothiophen-3-yl)-3-methylbenzonitrile (Scheme III, 13, X₁=4-cyano-2-methylphenyl) (2.4 g, yield 68%) as yellow oil. ¹H NMR (CD₃OD 400 MHz): δ 7.56 (s, 1H), 7.50-7.48 (m, 2H), 7.31 (d, J=3.2 Hz, 1H), 7.22 (d, J=7.6 Hz, 1H), 2.10 (s, 3H).

Step 2 of General Scheme III: Synthesis of (E)-ethyl 3-(4-(4-cyano-2-methylphenyl)thiophen-3-yl)acrylate To a solution of 4-(4-bromothiophen-3-yl)-3-methylbenzonitrile (2.4 g, 8.7 mmol) and ethyl 2-(tritylphosphinylidene)acetate (2.6 g, 26 mmol) in DMF (10 mL) was added Pd(OAc)₂ (194 mg, 0.87 mmol) and PPh₃ (228 mg, 0.87 mmol), and the mixture was stirred at 150° C. under nitrogen overnight. The mixture was diluted with EtOAc. The organic layer was washed with water and brine, dried over Na₂SO₄, concentrated in vacuo, and purified on silica gel column (PE: EtOAc=20:1) to give (E)-ethyl 3-(4-(4-cyano-2-methylphenyl)thiophen-3-yl)acrylate (Scheme III, 14, X₁=4-cyano-2-methylphenyl) (1 g, yield 39%) as yellow oil. ¹H NMR (CD₃OD 400 MHz): δ 8.03 (d, J=2.8 Hz, 1H), 7.71 (s, 1H), 7.64 (d, J=7.6 Hz, 1H), 7.39-7.34 (m, 2H), 7.28 (d, J=16 Hz, 1H), 6.06 (d, J=16.4 Hz, 1H), 4.15 (q, J=7.2 Hz, 2H), 2.15 (s, 3H), 1.24 (t, J=7.2 Hz, 3H).

Step 3 of General Scheme III: Synthesis of ethyl 3-(4-(4-cyano-2-methylphenyl)thiophen-3-yl)propanoate To a solution of (E)-ethyl 3-(4-(4-cyano-2-methylphenyl) thiophen-3-yl)acrylate (1 g, 3.4 mmol) in EtOH (20 mL) was added 10% Pd/C (w/w, 400 mg), and the mixture was stirred at room temperature under 1 atm of $H_2$ overnight. The reaction mixture was filtered, and concentrated to give ethyl 3-(4-(4-cyano-2-methylphenyl)thiophen-3-yl)propanoate (Scheme III, 15, $X_1$=4-cyano-2-methylphenyl) (0.9 g, yield 90%) as gray oil. $^1$H NMR (CD$_3$OD 400 MHz): δ 7.69 (s, 1H), 7.60 (dd, J=8 Hz, J=1.2 Hz, 1H), 7.34 (d, J=8 Hz, 1H), 7.26-7.23 (m, 2H), 4.05 (q, J=7.2 Hz, 2H), 2.67 (t, J=7.6 Hz, 2H), 2.45 (t, J=7.6 Hz, 2H), 2.19 (s, 3H), 1.19 (t, J=7.2 Hz, 3H).

Step 4 of General Scheme III: Synthesis of ethyl 3-(5-bromo-4-(4-cyano-2-methylphenyl)thiophen-3-yl)propanoate To a solution of compound 5 (500 mg, 1.7 mmol) in DMF (10 mL) was added NBS (296 mg, 1.7 mmol), and the resulting mixture was stirred at 100° C. overnight. When TLC showed the starting material was consumed. The mixture was diluted with EtOAc, washed with water and brine, concentrated, and purified by preparative HPLC to afford the desired ethyl 3-(5-bromo-4-(4-cyano-2-methylphenyl)thiophen-3-yl)propanoate (Scheme III, 16, $X_1$=4-cyano-2-methylphenyl) (15 mg, yield 2%) (the undesired isomer was isolated in 41% yield). $^1$H NMR (DMSO-d$_6$ 400 MHz): δ7.86 (s, 1H), 7.75 (d, J=7.6 Hz, 1H), 7.43 (s, 1H), 7.30 (d, J=8.0 Hz, 1H), 3.96 (q, J=7.2 Hz, 2H), 2.42 (s, 2H), 2.05 (s, 5H), 1.09 (t, J=7.2 Hz, 3H).

Step 5 of General Scheme III: Synthesis of 3-(4-(4-cyano-2-methylphenyl)-5-(4-methoxyphenyl) thiophen-3-yl)propanoic acid A mixture of ethyl 3-(5-bromo-4-(4-cyano-2-methylphenyl)thiophen-3-yl)propanoate (35 mg, 0.09 mmol), 4-methoxyphenylboronic acid (16 mg, 0.10 mmol), Na$_2$CO$_3$ (19 mg, 0.18 mmol), Pd(PPh$_3$)$_2$Cl$_2$ (6 mg, 0.009 mmol) in a mixture of dioxane and H$_2$O (5 mL, 4:1) was stirred at 100° C. overnight under nitrogen. The mixture was neutralized to pH=5, and extracted with EtOAc. The organic layer was concentrated, and purified by preparative TLC to give 3-(4-(4-cyano-2-methylphenyl)-5-(4-methoxyphenyl)thiophen-3-yl)propanoic acid (30 mg, yield 86%) as yellow oil.

Step 6 of General Scheme III: Synthesis of 3-(4-(4-carbamoyl-2-methylphenyl)-5-(4-methoxyphenyl) thiophen-3-yl)propanoic acid To a solution of 3-(4-(4-cyano-2-methylphenyl)-5-(4-methoxyphenyl)thiophen-3-yl)propanoic acid (30 mg, 0.08 mmol) in DMSO (5 mL) was added NaOH (6 mg, 0.16 mmol), and 30% H$_2$O$_2$ (9 mg, 0.08 mmol). The mixture was stirred at room temperature for 2 h, and purified by preparative HPLC to give 16 mg of the title compound, Example 14 (Scheme III, 17, $X_1$=4-carbamoyl-2-methylphenyl, $X_2$=4-methoxyphenyl) (yield 52%) as a white solid. $^1$H NMR (CD$_3$OD 400 MHz TMS): δ7.72 (s, 2H), 7.26 (d, J=8.4 Hz, 1H), 7.14 (s, 1H), 7.04 (d, J=8.8 Hz, 2H), 6.70 (d, J=8.4 Hz, 2H), 3.70 (s, 3H), 2.57 (t, J=7.2 Hz, 2H), 2.38 (t, J=8.0 Hz, 2H), 1.96 (s, 3H); MS (ESI): m/z 317.9 [M+23]$^+$.

Example 15

Synthesis of Intermediates referenced in the above Examples

Intermediate 1: 3,4-dibromothiophene-2-carbaldehyde

To a solution of diisopropylamine (1.3 g, 12.5 mmol) in 15 mL of anhydrous THF was added n-BuLi (4.0 mL, 2.5 M in hexane) at −78° C. After the mixture was stirred at −78° C. for 0.5 h 3,4-dibromothiophene (2 g, 8.3 mmol) in anhydrous THF (20 mL) was added. The mixture was stirred at −78° C. for 15 min., a solution of DMF (670 mg, 9.2 mmol) in THF (5 mL) was added. After being stirred at this temperature for 0.5 h, the mixture was stirred at room temperature for 2 hours. The mixture was quenched with NH$_4$Cl saturated solution, diluted with water, extracted with EtOAc, concentrated, and purified by column chromatography to give 3,4-dibromothiophene-2-carbaldehyde (1.0 g, yield 45%).

Intermediate 2: 2-methyl-1-(4-(4,4,5,5-tetramethyl-1, 3,2-dioxaborolan-2-yl)phenyl)-1H-imidazole Step 1: A mixture of 1-fluoro-4-nitrobenzene (10 g, 70.9 mmol), 2-methyl-1H-imidazole (5.8 g, 70.9 mmol), and Cs$_2$CO$_3$ (34.7 g, 106.4 mmol) in degassed DMF (200 mL) was heated at 100° C. under nitrogen overnight. When TLC indicated that 1-fluoro-4-nitrobenzene was consumed, the reaction mixture was concentrated in vacuo. The residue was diluted with water (300 mL), and a grey precipitate was formed and was isolated to give 2-methyl-1-(4-nitrophenyl)-1H-imidazole (12.8 g, yield 89%).

Step 2: To a solution 2-methyl-1-(4-nitrophenyl)-1H-imidazole (12.8 g, 63 mmol) in MeOH (150 mL) was added Pd/C (3 g). The resulting mixture was stirred at room temperature for 8 hours under hydrogen. When TLC indicated the starting material was consumed, the mixture was filtered and concentrated in vacuo to give 4-(2-methyl-1H-imidazol-1-yl)aniline (10 g, yield 92%).

Step 3: To a solution of 4-(2-methyl-1H-imidazol-1-yl) aniline (10 g, 57.8 mmol) in 100 mL of HBr solution was added a solution of NaNO$_2$ (5.2 g, 75.1 mmol) in H$_2$O (60 mL) at 0° C. Stirred at this temperature for 20 min., then poured the mixture into a solution of CuBr (58 g, 404 mmol) in HBr solution (200 mL) at 0° C., and stirred for 30 min., diluted with water, and stirred at room temperature for 1 hour. The precipitate was separated out, and evaporated in vacuo to give 28 g of crude product, which was purified by Prep-HPLC to obtain 1-(4-bromophenyl)-2-methyl-1H-imidazole (7 g, yield 51%).

Step 4: A mixture of 1-(4-bromophenyl)-2-methyl-1H-imidazole (3.6 g, 15.3 mmol), 4,4,4',4',5,5,5',5'-octamethyl-2,2'-bi(1,3,2-dioxaborolane) (4.3 g, 16.8 mmol), KOAc (3.0 g, 30.5 mmol), and Pd(dppf)Cl$_2$ (559 mg, 0.76 mmol) in DMF (40 mL) was stirred at 100° C. overnight. When TLC indicated the starting material was consumed, the mixture was concentrated and purified by column chromatography (PE:EtOAc=1:2) to afford 2-methyl-1-(4-(4,4,5,5-tetramethyl-1, 3,2-dioxaborolan-2-yl)phenyl)-1H-imidazole (1.1 g, yield 26%).

Intermediate 3: 4-(4-bromo-5-formylthiophen-3-yl)benzonitrile

To a solution of diisopropylamine (1.2 g, 11.4 mmol) in 20 mL of anhydrous THF was added n-BuLi (3.7 mL, 2.5 M in hexane) at −78° C. After the mixture was stirred at this temperature for 0.5 h, a solution of 4-(4-bromothiophen-3-yl) benzonitrile (prepared in Step 1 of Compound 2) (2.0 g, 7.6 mmol) in anhydrous THF (20 mL) was added dropwise. The mixture was stirred at −78° C. for 15 min., a solution of DMF (611 mg, 8.4 mmol) in THF (5 mL) was added. The reaction mixture was stirred at −78° C. for 0.5 h, and at room temperature for 2 h. The mixture was quenched with saturated $NH_4Cl$ aqueous solution, extracted with EtOAc, concentrated, and purified by column chromatography on silica gel to give 4-(4-bromo-5-formylthiophen-3-yl)benzonitrile (600 mg, yield 27%).

Intermediate 4: N-(4-(4-bromo-2-formylthiophen-3-yl)-3-methylphenyl)methanesulfonamide Step 1: To the solution of N-(4-bromo-3-methylphenyl) methanesulfonamide (11.5 g, 43 mmol) in DMF were added bis(pinacolato)diboron (12 g, 47.3 mmol) and KOAc (8.4 g, 86 mmol), the mixture was degassed with $N_2$, and $PdCl_2$ (dppf) (2 g, 2.7 mmol) was added, then the mixture was degassed again, and the resulting mixture was heated to 100° C. under $N_2$ overnight. The reaction solution was diluted with EtOAc (500 mL), and filtrated by a celite, washed with EtOAc, the filtrate was concentrated under reduced pressure. The residue was purified by column chromatography to give N-(3-methyl-4-(4,4,5,5-tetramethyl-1,3,2-dioxaborolan-2-yl)phenyl)methanesulfonamide (8.2 g, yield 60%).

Step 2: To the solution of Intermediate 1 (4 g, 15 mmol) in a mixture of DME and $H_2O$ (150 mL/50 mL) were added N-(3-methyl-4-(4,4,5,5-tetramethyl-1,3,2-dioxaborolan-2-yl)phenyl)methanesulfonamide (3.6 g, 1.65 mmol) and $Na_2CO_3$ (2.8 g, 3.1 mmol), the mixture was degassed with $N_2$, and $Pd(PPh_3)_4$ (500 mg) was added, then the mixture was heated to 100° C. under $N_2$ overnight. The reaction solution was concentrated to remove the organic solution, then the aqueous layer was extracted with EtOAc (100 mL×3). The combined organic layers were washed with brine, dried over $Na_2SO_4$, concentrated under reduced pressure, the residue was purified by column chromatography to give N-(4-(4-bromo-2-formylthiophen-3-yl)-3-methylphenyl)methanesulfonamide (2.0 g, yield 35.7%).

Intermediate 5: 2-methyl-1-(5-(tributylstannyl) thiophen-2-yl)-1H-imidazole

Step 1: To the solution of 2,5-dibromothiophene (20 g, 82.6 mmol) and 2-methyl-1H-imidazole (4.1 g, 50 mmol) in DMSO (100 mL) was added CuI (3.14 g, 16.5 mmol), L-proline (0.95 g, 8.3 mmol), $K_2CO_3$ (22.9 g, 0.165 mol), the resultant mixture was heated to 100° C. under $N_2$ balloon protection overnight. The reaction mixture was filtrated and the filtrate was poured into water, extracted with EtOAc (300 mL×5). The combined organic layers were washed with brine, dried over $Na_2SO_4$, and then filtrated, the filtrate was concentrated under reduced pressure, the residue was purified by column chromatography to give desired 1-(5-bromothiophen-2-yl)-2-methyl-1H-imidazole (3.8 g, yield 31.2%).

Step 2: To the solution of 1-(5-bromothiophen-2-yl)-2-methyl-1H-imidazole (2 g, 8.3 mmol) in dried THF was added dropwise n-BuLi (2.5 M in hexane, 4 mL, 10 mmol) at −78° C., the mixture was stirred at −78° C. for 30 min. A solution of tributyltin chloride (4.6 g, 0.96 mmol) in THF was added dropwise, the solution was stirred at −78° C. for 1 hour, and the reaction solution was allowed to warm to room temperature and stirred for 1 hour. The reaction solution was poured into $NH_4Cl$ aqueous solution, the mixture was extracted with EtOAc (100 mL×3). The organic layer was washed with brine, dried over $Na_2SO_4$, then concentrated under reduced pressure, and the residue was purified by column chromatography to give 2-methyl-1-(5-(tributylstannyl) thiophen-2-yl)-1H-imidazole as a yellow oil (1.2 g, yield 31.8%).

Example 16

GSNOR Assays

Various compounds were tested in vitro for their ability to inhibit GSNOR activity. GSNOR inhibitor compounds Examples 1-14 had an $IC_{50}$ of about <10 µM. GSNOR inhibitor compounds Examples 1, 2, 4, 7-9, 11-13, 14 had an $IC_{50}$ of about less than 1.0 µM.

GSNOR expression and purification is described in Biochemistry 2000, 39, 10720-10729.

GSNOR Fermentation

Pre-cultures were grown from stabs of a GSNOR glycerol stock in 2XYT media containing 100 ug/ml ampicillin after an overnight incubation at 37° C. Cells were then added to fresh 2XYT (4L) containing ampicillin and grown to an OD ($A_{600}$) of 0.6-0.9 at 37° C. before induction. GSNOR expression was induced with 0.1% arabinose in an overnight incubation at 20° C.

GSNOR Purification

*E. coli* cell paste was lysed by nitrogen cavitation and the clarified lysate purified by Ni affinity chromatography on an AKTA FPLC (Amersham Pharmacia). The column was eluted in 20 mM Tris pH 8.0/250 mM NaCl with a 0-500 mM imidazole gradient. Eluted GSNOR fractions containing the Smt-GSNOR fusion were digested overnight with Ulp-1 at 4° C. to remove the affinity tag then re-run on the Ni column under the same conditions. GSNOR was recovered in the flowthrough fraction and for crystallography is further purified by Q-Sepharose and Heparin flowthrough chromatography in 20 mM Tris pH 8.0, 1 mM DTT, 10 uM $ZnSO_4$.

GSNOR Assay

GSNO and enzyme/NADH Solutions are made up fresh each day. The solutions are filtered and allowed to warm to room temperature. GSNO solution: 100 mM NaPO4 (pH 7.4), 0.480 mM GSNO. 396 µL of GSNO Solution is added to a cuvette followed by 8 µL of test compound in DMSO (or DMSO only for full reaction control) and mixed with the pipette tip. Compounds to be tested are made up at a stock concentration of 10 mM in 100% DMSO. 2 fold serial dilutions are done in 100% DMSO. 8 µL of each dilution are added to an assay so that the final concentration of DMSO in the assay is 1%. The concentrations of compounds tested range from 100 to 0.003 µM. Enzyme/NADH solution: 100 mM $NaPO_4$ (pH 7.4), 0.600 mM NADH, 1.0 µg/mL GSNO Reductase. 396 µL of the Enzyme/NADH solution is added to the cuvette to start the reaction. The cuvette is placed in the Cary 3E UV/Visible Spectrophotometer and the change in 340 nm absorbance/min at 25° C. is recorded for 3 minutes. The assays are done in triplicate for each compound concentration. $IC_{50}$'s for each compound are calculated using the standard curve analysis in the Enzyme Kinetics Module of SigmaPlot.

Final assay conditions: 100 mM $NaPO_4$, pH 7.4, 0.240 mM GSNO, 0.300 mM NADH, 0.5 µg/mL GSNO Reductase, and 1% DMSO. Final volume: 800 µL/cuvette.

Example 17

Efficacy of GSNORi in Experimental Asthma

Experimental Asthma Model:
A mouse model of ovalbumin (OVA)-induced asthma can be used to screen GSNOR inhibitors for efficacy against methacholine (MCh)-induced bronchoconstriction/airway hyper-responsiveness. This is a widely used and well characterized model that presents with an acute, allergic asthma phenotype with similarities to human asthma. Efficacy of GSNOR inhibitors is assessed using a protocol in which GSNOR inhibitors are administered after OVA sensitization and airway challenge, and prior to challenge with MCh. Bronchoconstriction in response to challenge with increasing doses of MCh is assessed using whole body plethysmography ($P_{enh}$; Buxco). The amount of eosinophil infiltrate into the bronchoaveolar lavage fluid (BALF) is also determined as a measure of lung inflammation. The effect of GSNOR inhibitors is compared to vehicles and to Combivent (inhaled; 1H) as the positive control.

Materials and Method

Allergen Sensitization and Challenge Protocol

OVA (500 μg/ml) in PBS is mixed with equal volumes of 10% (w/v) aluminum potassium sulfate in distilled water and incubated for 60 min. at room temperature after adjustment to pH 6.5 using 10 N NaOH. After centrifugation at 750×g for 5 min, the OVA/alum pellet is resuspended to the original volume in distilled water. Mice received an intraperitoneal (IP) injection of 100 μg OVA (0.2 mL of 500 μg/mL in normal saline) complexed with alum on day 0. Mice are anesthetized by IP injection of a 0.2-mL mixture of ketamine and xylazine (0.44 and 6.3 mg/mL, respectively) in normal saline and are placed on a board in the supine position. Two hundred fifty micrograms (100 μl of a 2.5 mg/ml) of OVA (on day 8) and 125 μg (50 μl of 2.5 mg/ml) OVA (on days 15, 18, and 21) are placed on the back of the tongue of each animal.

Pulmonary Function Testing (Penh)

In vivo airway responsiveness to methacholine is measured 24 h after the last OVA challenge in conscious, freely moving, spontaneously breathing mice with whole body plethysmography using a Buxco chamber (Wilmington, N.C.). Mice are challenged with aerosolized saline or increasing doses of methacholine (5, 20, and 50 mg/mL) generated by an ultrasonic nebulizer for 2 min. The degree of bronchoconstriction is expressed as enhanced pause ($P_{enh}$), a calculated dimensionless value, which correlates with the measurement of airway resistance, impedance, and intrapleural pressure in the same mouse. $P_{enh}$ readings are taken and averaged for 4 min. after each nebulization challenge. $P_{enh}$ is calculated as follows: $P_{enh}=[(T_e/T_r-1)\times(PEF/PIF)]$, where $T_e$ is expiration time, $T_r$ is relaxation time, PEF is peak expiratory flow, and PIF is peak inspiratory flow×0.67 coefficient. The time for the box pressure to change from a maximum to a user-defined percentage of the maximum represents the relaxation time. The $T_r$ measurement begins at the maximum box pressure and ends at 40%.

Eosinophil Infiltrate in BALF

After measurement of airway hyper-reactivity, the mice are exsanguinated by cardiac puncture, and then BALF is collected from either both lungs or from the right lung after tying off the left lung at the mainstem bronchus. Total BALF cells are counted from a 0.05 mL aliquot, and the remaining fluid is centrifuged at 200×g for 10 min at 4° C. Cell pellets are resuspended in saline containing 10% BSA with smears made on glass slides. Eosinophils are stained for 5 min. with 0.05% aqueous eosin and 5% acetone in distilled water, rinsed with distilled water, and counterstained with 0.07% methylene blue. Alternatively, eosinophils and other leukocytes are stained with DiffQuik.

GSNOR Inhibitors and Controls

GSNOR inhibitors are reconstituted in phosphate buffered saline (PBS), pH 7.4, or 0.5% w/v carboxy methylcellulose at concentrations ranging from 0.00005 to 3 mg/mL. GSNOR inhibitors are administered to mice (10 mL/kg) as a single dose or multiple dose either intravenously (IV) or orally via gavage. Dosing is performed from 30 min. to 72 h prior to MCh challenge. Effect of GSNOR inhibitors are compared to vehicle dosed in the same manner.

Combivent is used as the positive control in all studies. Combivent (Boehringer Ingelheim) is administered to the lung using the inhaler device supplied with the product, but adapted for administration to mice, using a pipet tip. Combivent is administered 48 h, 24 h, and 1 h prior to MCh challenge. Each puff (or dose) of Combivent provides a dose of 18 μg ipatropium bromide (IpBr) and 103 μg albuterol sulfate or approximately 0.9 mg/kg IpBr and 5 mg/kg albuterol.

Statistical Analyses

Area under the curve values for $P_{enh}$ across baseline, saline, and increasing doses of MCh challenge are calculated using GraphPad Prism 5.0 (San Diego, Calif.) and expressed as a percent of the respective (IV or orally administered) vehicle control. Statistical differences among treatment groups and the respective vehicle control group within each study are calculated using one-way ANOVA, Dunnetts or Bonferroni post-hoc tests or t-test (JMP 8.0, SAS Institute, Cary, N.C. or Microsoft Excel). A p value of <0.05 among the treatment groups and the respective vehicle control group is considered significantly different.

Example 18

Mouse Pharmacokinetic (PK) Study

Experimental Model

The mouse can be used to determine the pharmacokinetics of compounds of the invention. This species is widely used to assess the bioavailability of compounds by administering both oral (PO) and intravenous (IV) test articles. Efficacy of the compounds of the invention is compared by assessing plasma exposure in male BALB/c mice either via IV or PO administration at the times of peak activity.

Materials and Methods

IV Administration of Compounds of the Invention

Compounds of the invention are reconstituted in a phosphate buffered saline (PBS)/10% Solutol (HS 15) clear solution resulting in a concentration of 0.2 mg/mL and administered to mice (2 mg/kg) as a single IV dose. Animals are dosed via the lateral tail vein. Blood samples are collected at designated time points (0.083, 0.25, 0.5, 1, 2, 4, 8, 16, 24 hours) by cardiac puncture under isoflurane anesthesia (up to 1 mL blood per animal). The blood is collected into tubes containing Li-Heparin. The blood samples are kept on ice until centrifugation within approximately 30 minutes of collection. The plasma is transferred into labeled polypropylene tubes and frozen at −70° C. until analyzed by LC/MS/MS.

PO Administration of Compounds of the Invention

The compounds of the invention are reconstituted in 40% Propylene Glycol/40% Propylene Carbonate/20% of a 5% Sucrose clear solution resulting in a concentration of 2 mg/mL and administered to mice (10 mg/kg) as a single oral dose via gavage. Blood samples are collected at 0.25, 0.5, 1, 2, 4, 8, 12, 16, 20 and 24 hours post dose by cardiac puncture under isoflurane anesthesia. The blood is collected in tubes containing Li-Heparin. The blood samples are kept on ice until centrifugation within approximately 30 minutes of collection. The plasma is transferred into labeled polypropylene tubes and frozen at −70° C. until analyzed by LC/MS/MS.

LC/MS/MS Analysis

Plasma samples at each timepoint are analyzed using a LC-MS/MS with a lower limit of quantification (LLOQ) of 1 ng/mL. Plasma is analyzed to determine the amount of the compound of the invention in each sample and regression curves generated for each compounds of the invention in the relevant matrixes.

WinNonlin analysis is used for calculating PK parameters for both the IV and PO administrations:

PK parameters for IV portion—$AUC_{last}$; $AUC_{INF}$; T1/2; Cl; Vss; $C_{max}$; MRT PK parameters for PO portion—$AUC_{last}$; $AUC_{INF}$; T1/2; $C_{max}$; Cl, MRT.

In addition to the above PK parameters, bioavailability (% F) can be calculated.

Example 19

Efficacy of GSNOR Inhibitors in Experimental Inflammatory Bowel Disease (IBD)

Overview of the Models:

Acute and chronic models of dextran sodium sulfate (DSS)-induced IBD in mice can be used to explore efficacy of GSNORi against this disease. Acute and chronic DSS-induced IBD are widely used and well characterized models that induce pathological changes in the colon similar to those observed in the human disease. In these models and in human disease, epithelial cells within the crypts of the colon are disrupted, leading to dysfunction of the epithelial barrier and the ensuing tissue inflammation, edema, and ulceration. GSNORi therapy may benefit IBD by restoring s-nitrosoglutathione (GSNO) levels, and thus prevent or reverse the epithelial barrier dysfunction.

Acute Prophylactic Model:

Experimental IBD is induced by administration of DSS in the drinking water of male C57B1/6 mice (N=8 to 10 mice per group) for 6 consecutive days. GSNORi is dosed orally at doses of 0.1 to 10 mg/kg/day for 10 days starting two days prior to and continuing two days post DSS exposure. Two days post DSS exposure, the effect of GSNORi is assessed in a blinded fashion via endoscopy and histopathology using a five point scale ranging from a score=0 (normal tissue) through a score=4 (ulcerative tissue damage and marked pathological changes). Levels of circulating cytokines involved in inflammatory pathways are also assessed. The effect of GSNORi is compared to vehicle treated controls. The corticosteroid, prednisolone, is used as the positive control in this study and is administered daily at 3 mg/kg/day via oral dosing. Naïve mice (N=5) are also assessed as a normal tissue control.

Chronic Treatment Model:

Experimental IBD is induced by administration of DSS in the drinking water of male C57B1/6 mice (N=10 to 12 mice per group) for 6 consecutive days. GSNORi is dosed orally at doses of 10 mg/kg/day for 14 days starting one day after cessation of DSS exposure. Efficacy of GSNORi is assessed in a blinded fashion via endoscopy after 7 days and 14 days of GSNORi dosing and via histopathology after 14 days of GSNORi dosing using a five point scale ranging from a score=0 (normal tissue) through a score=4 (ulcerative tissue damage and marked pathological changes). Levels of circulating cytokines involved in inflammatory pathways are also assessed. The effect of GSNORi is compared to vehicle treated controls. The corticosteroid, prednisolone, is used as the positive control in this study and is administered daily at 3 mg/kg/day via oral dosing. Naïve mice (N=5) are also assessed as a normal tissue control.

Example 20

Efficacy of GSNOR Inhibitors in Experimental Chronic Obstructive Pulmonary Disease (COPD)

Short Duration Cigarette Smoke COPD Models

The efficacy of GSNOR inhibitors can be assessed in a mouse model of chronic obstructive pulmonary disease (COPD) induced by short duration (4 days or 11 days) of exposure to cigarette smoke. Infiltration of inflammatory cells into the bronchoalveolar lavage fluid (BALF) and BALF levels of chemokines involved in inflammation and tissue turnover/repair are measured to assess the influences of GSNOR inhibitors on some of the early events associated with the initiation and progression of COPD.

Overview of the Models:

Efficacy of GSNOR inhibitors against COPD is explored using acute (4 day) and subchronic (11 day) models of cigarette smoke-induced COPD in mice. Exposure of animals to cigarette smoke provides a model of COPD in which injury is induced by the same causative agent as in human disease and in which injury exhibits similarities to the human disease, including airway obstruction, airspace enlargement, and involvement of inflammatory responses in these pathologies. In animal models, changes in lung pathology are only evident after extended (several months) duration of exposure to cigarette smoke, thus making chronic models prohibitive as effective screening tools. More recently, models exploring inflammatory responses after short duration (2 weeks or less) of smoke exposure in mice have been utilized as tools for screening efficacy and mechanisms of action of novel therapeutics against COPD. The key roles of inflammation in the initiation and progression of COPD, make these short duration models relevant for initial tests of efficacy of novel therapeutics.

Acute (4 Day) Smoke Exposure Model

Female C57B1/6 mice (N=8 per group) are exposed to cigarette smoke using a whole body exposure chamber. Mice are exposed daily for 4 consecutive days to 4 cycles of smoke from 6 sequential cigarettes (Kentucky 3R4F without filter) with a 30 minute smoke free interval between cycles. GSNOR inhibitors are administered daily via oral dosing at 10 mg/kg/day for 7 days starting 2 days prior to smoke exposure and continuing 1 day post-exposure. The effects of GSNOR inhibitors are assessed by quantization of the numbers of total cells, leukocytes, and leukocytes differentials in the BALF via light microscopy and the levels of BALF chemokines via ELISA at approximately 24 h after the last smoke exposure. The effect of GSNOR inhibitors are compared to vehicle treated controls. The PDE4 inhibitor, roflumilast, is used as the positive control for the study. A group of naïve mice (N=8) is exposed to air and used as a negative control for the study.

Subchronic (11 Day) Smoke Exposure Model

Female C57B1/6 Mice (N=10 Per group) are exposed to cigarette smoke generated from Marlboro 100 cigarettes without filters. Exposure times are 25 min. on study day 1, 35 min on study day 2, and 45 min. on study days 3 to 11. GSNOR inhibitors are administered one hour prior to smoke exposure on each day. GSNOR inhibitors are dosed orally at 1 to 10 mg/kg/day for 11 days. The effects of GSNOR inhibitors are assessed by quantization of the number of total cells, and leukocytes differentials in the BALF via light microscopy at 24 h after the last exposure. The effect of GSNOR inhibitors are compared to vehicle treated controls and expressed as percent inhibition of the cigarette smoke induced increases in BALF cell numbers. Roflumilast is used as the positive control for the study and is dosed at 5 mg/kg/day. A group of naïve mice (N=10) is exposed to air and dosed with vehicle as a negative control for the study.

It will be apparent to those skilled in the art that various modifications and variations can be made in the methods and compositions of the present invention without departing from the spirit or scope of the invention.

What is claimed is:

1. A compound of Formula I or a pharmaceutically acceptable salt or stereoisomer thereof:

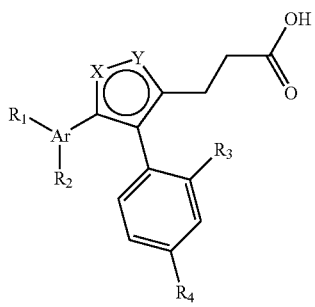

wherein:
X and Y are selected from the group consisting of S or CH, provided that when X is S, Y must be CH and when X is CH, Y must be S;
Ar is selected from the group consisting of phenyl and thiophen-yl;
$R_1$ is selected from the group consisting of hydrogen, unsubstituted imidazolyl, substituted imidazolyl, carbamoyl, chloro, bromo, fluoro, hydroxy, and methoxy;
$R_2$ is selected from the group consisting of hydrogen, methyl, chloro, fluoro, hydroxy, methoxy, ethoxy, propoxy, carbamoyl, dimethylamino, amino, formamido, and trifluoromethyl;
$R_3$ is selected from the group consisting of hydrogen, methyl, methoxy, chloro, and fluoro; and
$R_4$ is selected from the group consisting of $CONH_2$, $NHSO_2CH_3$, hydroxy, chloro, and substituted and unsubstituted imidazolyl.

2. The compound of claim 1 wherein Ar is selected from the group consisting of

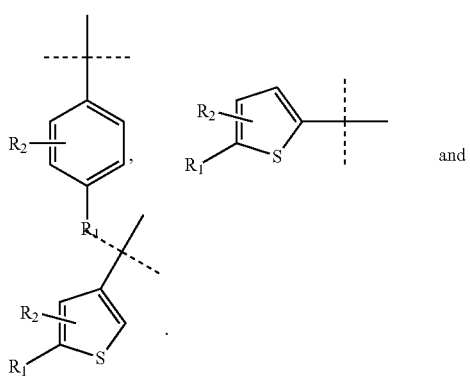

3. The compound of claim 2 wherein $R_1$ is

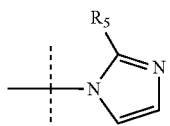

wherein $R_5$ is selected from the group consisting of hydrogen, methyl and ethyl.

4. The compound of claim 2 wherein $ArR_1R_2$ is selected from the group consisting of 4-methoxyphenyl, 4-chloro-2-methoxyphenyl, 4-hydroxyphenyl, 4-carbamoylphenyl, and 4-bromophenyl.

5. The compound of claim 1 wherein $R_3$ is selected from the group consisting of hydrogen, methyl, and methoxy.

6. A compound of claim 1 wherein the compound is a compound of Formula II:

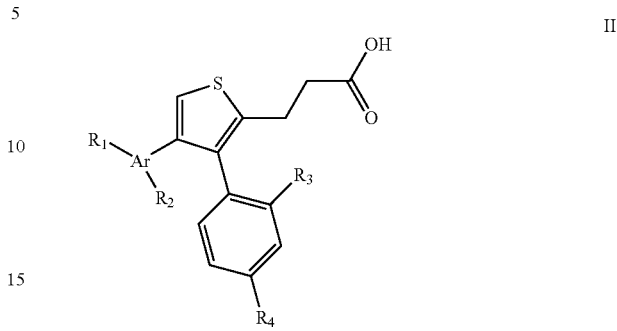

wherein:
Ar is selected from the group consisting of phenyl and thiophen-yl;
$R_1$ is selected from the group consisting of hydrogen, unsubstituted imidazolyl, substituted imidazolyl, carbamoyl, chloro, bromo, fluoro, hydroxy, and methoxy;
$R_2$ is selected from the group consisting of hydrogen, methyl, chloro, fluoro, hydroxy, methoxy, ethoxy, propoxy, carbamoyl, dimethylamino, amino, formamido, and trifluoromethyl; and
$R_3$ is selected from the group consisting of hydrogen, methyl, methoxy, chloro, and fluoro; and
$R_4$ is selected from the group consisting of $CONH_2$, $NHSO_2CH_3$, hydroxy, chloro, and substituted and unsubstituted imidazolyl.

7. The compound of claim 6 wherein Ar is selected from the group consisting of

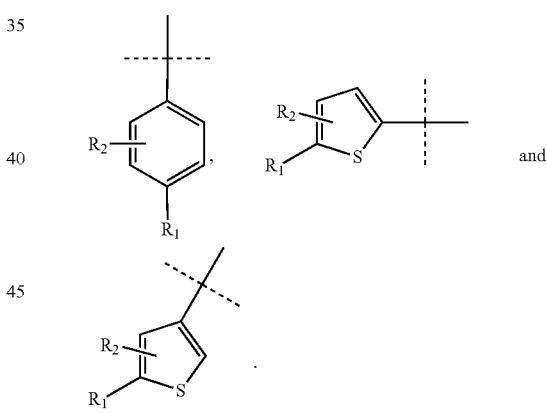

8. The compound of claim 7 wherein $R_1$ is

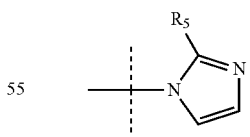

wherein $R_5$ is selected from the group consisting of hydrogen, methyl and ethyl.

9. The compound of claim 7 wherein $ArR_1R_2$ is selected from the group consisting of 4-methoxyphenyl, 4-chloro-2-methoxyphenyl, 4-hydroxyphenyl, 4-carbamoylphenyl, and 4-bromophenyl.

10. The compound of claim 6 wherein $R_3$ is selected from the group consisting of hydrogen, methyl, and methoxy.

11. The compound of claim 6 selected from the group consisting of 3-(3-(4-carbamoyl-2-methylphenyl)-4-(4-methoxyphenyl)thiophen-2-yl)propanoic acid;
3-(3-(4-carbamoylphenyl)-4-(4-chloro-2-methoxyphenyl)thiophen-2-yl)propanoic acid;
3-(3-(4-chloro-2-methoxyphenyl)-4-(4-hydroxyphenyl)thiophen-2-yl)propanoic acid;
3-(4-(4-chloro-2-methoxyphenyl)-3-(4-hydroxyphenyl)thiophen-2-yl)propanoic acid;
3-(4-(4-chloro-2-methoxyphenyl)-3-(4-(methylsulfonamido)phenyl)thiophen-2-yl)propanoic acid;
3-(4-(4-carbamoylphenyl)-3-(4-(2-methyl-1H-imidazol-1-yl)phenyl)thiophen-2-yl)propanoic acid;
3-(3-(4-carbamoyl-2-methylphenyl)-4-(4-(2-methyl-1H-imidazol-1-yl)phenyl)thiophen-2-yl)propanoic acid;
3-(3-(4-carbamoylphenyl)-4-(4-(2-methyl-1H-imidazol-1-yl)phenyl)thiophen-2-yl)propanoic acid;
3-(4-(4-(2-methyl-1H-imidazol-1-yl)phenyl)-3-(2-methyl-4-(methylsulfonamido)phenyl)thiophen-2-yl)propanoic acid;
3-(4-(4-chloro-2-methoxyphenyl)-3-(2-methyl-4-(methylsulfonamido)phenyl)thiophen-2-yl)propanoic acid;
3-(4'-(4-carbamoyl-2-methylphenyl)-5-(2-methyl-1H-imidazol-1-yl)-2,3'-bithiophen-5'-yl)propanoic acid;
3-(5-(2-methyl-1H-imidazol-1-yl)-4'-(2-methyl-4-(methylsulfonamido)phenyl)-2,3'-bithiophen-5'-yl)propanoic acid; and
3-(4-(4-bromophenyl)-3-(4-carbamoyl-2-methylphenyl)thiophen-2-yl)propanoic acid.

12. A compound of claim 1 wherein the compound is a compound of Formula III:

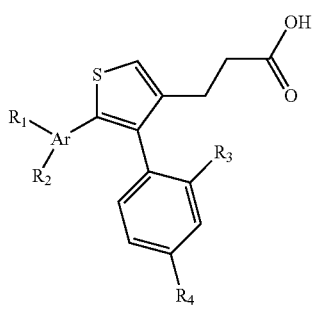

III wherein:
Ar is selected from the group consisting of phenyl and thiophen-yl;
$R_1$ is selected from the group consisting of hydrogen, unsubstituted imidazolyl, substituted imidazolyl, carbamoyl, chloro, bromo, fluoro, hydroxy, and methoxy;
$R_2$ is selected from the group consisting of hydrogen, methyl, chloro, fluoro, hydroxy, methoxy, ethoxy, propoxy, carbamoyl, dimethylamino, amino, formamido, and trifluoromethyl;
$R_3$ is selected from the group consisting of hydrogen, methyl, methoxy, chloro, and fluoro; and
$R_4$ is selected from the group consisting of $CONH_2$, $NHSO_2CH_3$, hydroxy, chloro, and substituted and unsubstituted imidazolyl.

13. The compound of claim 12 wherein Ar is selected from the group consisting of

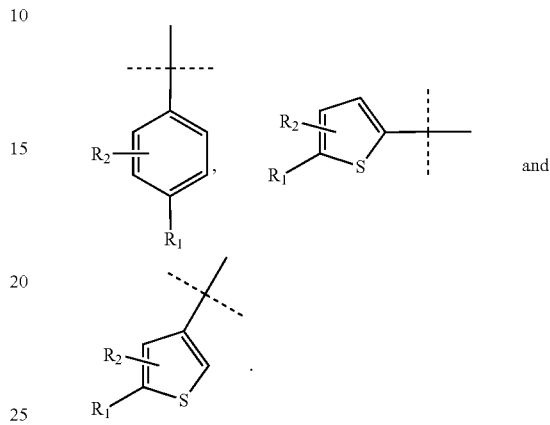

and

14. The compound of claim 13 wherein $R_1$ is

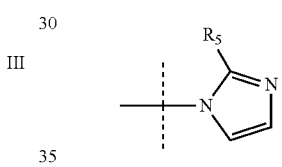

wherein $R_5$ is selected from the group consisting of hydrogen, methyl and ethyl.

15. The compound of claim 13 wherein $ArR_1R_2$ is selected from the group consisting of 4-methoxyphenyl, 4-chloro-2-methoxyphenyl, 4-hydroxyphenyl, 4-carbamoylphenyl, and 4-bromophenyl.

16. The compound of claim 12 wherein $R_3$ is selected from the group consisting of hydrogen, methyl, and methoxy.

17. The compound of claim 12 selected from the group consisting of 3-(4-(4-carbamoyl-2-methylphenyl)-5-(4-methoxyphenyl)thiophen-3-yl)propanoic acid.

18. A pharmaceutical composition comprising a therapeutically effective amount of a compound of Formula I according to claim 1 together with a pharmaceutically accepted carrier or excipient.

* * * * *